(12) United States Patent
Martin et al.

(10) Patent No.: US 6,734,289 B2
(45) Date of Patent: May 11, 2004

(54) GASTROKINES AND DERIVED PEPTIDES INCLUDING INHIBITORS

(75) Inventors: Terence Martin, Chicago, IL (US); F. Gary Toback, Chicago, IL (US); C. Thomas Powell, Bratenahl, OH (US); Kan Agarwal, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/821,726

(22) Filed: Mar. 29, 2001

(65) Prior Publication Data

US 2003/0017548 A1 Jan. 23, 2003

(51) Int. Cl.$^7$ .......................... A61K 38/17; A61K 38/04
(52) U.S. Cl. ....................... 530/399; 530/324; 530/325; 530/326; 514/12; 514/13; 514/14
(58) Field of Search ................................. 530/324, 325, 530/326, 399; 514/12, 13, 14

(56) References Cited

FOREIGN PATENT DOCUMENTS

| EP | 0 972 830 A1 | | 1/2000 |
|---|---|---|---|
| WO | WO 99/07840 | * | 2/1999 |

OTHER PUBLICATIONS

Hayashizaki et al. (Feb. 8, 2001) Nature 409:685–690.*
Kawai et al., Functional annotation of a full–length mouse cDNA collection, 2001, Nature, vol. 409, pp. 685–690.*
Clackson et al., A hot spot of binding energy in a hormone–receptor interface, 1995, Science, vol. 267, pp. 383–386.*
Tarnawski, Cellular and molecular mechanisms of ulcer healing, 1997, Drugs of Today, vol. 33, pp. 697–706.*
Schmassmann et al., Roles of hepatocyte growth factor and its receptor met during gastric ulcer healing in rats, 1997, Gastroenterology, vol. 113, pp. 1858–1872.*
Aithal, N.H., et al. (1994) "Glyceraldehyde–3–phosphate Dehydrogenase Modifier Protein is Associated with Microtubules in Kidney Epithelial Cells." *Am. J. Physiol.* 266:F612–619.
Altschul, S.F., et al. (1997) "Gapped BLAST and PSI–BLAST: a New Generation of Protein Database Search Programs." *Nuc. Acids Res.* 25 (17):3389–3402.
Baczako, K, et al. (1995) "Lectin–Binding Properties of the Antral and Body Surface Mucosa in the Human Stomach—Are the Differences Relevant for *Helicobacter Pylori* Affinity?" *J. Pathol.* 176:77–86.
Blaser, M.J. (1987) "Gastric *Campylobacter*–like Organisms, Gastritis, and Peptic Ulcer Disease." *Gastroenterol.* 93:371–383.
Boman, H.G. (1995) "Peptide Antibiotics and Their Role in Innate Immunity." *Ann. Rev. Immunol.* 13:61–92.
Cohen, G.B., et al. (1995) "Modular Binding Domains in Signal Transduction Proteins." *Cell* 80:237–248.

Cregg, J.M., et al. (1993) "Recent Advances in the Expression of Foreign Genes in *Pichia pastoris.*" *Bio/Technol.* 11:905–910.
Dignass, A.U., et al. (1998) "Adenine Nucleotides Modulate Epithelial Wound Healing In Vitro." *Eur. J. Clin. Invest.* 28:554–561.
Falk, P., et al. (1993) "An In vitro Adherence Assay Reveals That *Helicobacter Pylori* Exhibits Cell Lineage–Specific Tropism in the Human Gastric Epithelium." *Proc. Nat. Acad. Sci. USA* 90:2035–2039.
Goodwin, C.S., et al., (1986) "*Campylocbacter pyloridis*, Gastritis, and Peptic Ulceration." *J. Clin. Pathol.* 39:353–356.
Hasty, P., et al. (1991) "The Length of Homology Required for Gene Targeting in Embryonic Stem Cells." *Mol. Cell. Biol.* 11:5586–5591.
Houston, M.E., et al. (1996) "Lactam Bridge Stabilization of a α–Helices: The Role of Hydrophobicity in Controlling Dimeric versus Monomeric α–Helices." *Biochem.* 35:10041–10050.
Janknecht, R., et al. (1991) "Rapid and Efficient Purification of Native Histidine–Tagged Protein Expressed by Recombinant Vaccinia Virus." *Proc. Nat. Acad. Sci. USA* 88:8972–8976.
Jeon, C.J., et al. (1994) "The Transcription Factor TFIIS Zinc Ribbon Dipeptide Asp–Glu is Critical for Stimulation of Elongation and RNA Cleavage by RNA Polymerase II." *Proc. Nat. Acad. Sci. USA* 91:9106–9110.
Johnson, F.R. and McMinn, R.M.H. (1970) "Microscopic Structure of Pyloric Epithelium of the Cat." *J. Anat.* 107:67–86.
Kartha, S. and Toback, F.G. (1985) "Purine Nucleotides Stimulate DNA Synthesis in Kidney Epithelial Cells in Culture." *Am. J. Physiol.* 249:F967–F972.
Lacy, E.R. (1998) "Epithelial Restitution in the Gastrointestinal Tract." *J. Clin. Gastroenterol.* 10(Suppll):s72–s77.
Lieske, J.C., et al. (1994) "Renal Epithelial Cells Rapidly Bind and Internalize Calcium Oxalate Monohydrate Crystals." *Proc. Natl. Acad. Sci. USA* 91:6987–6991.s.

(List continued on next page.)

*Primary Examiner*—David Guzo
*Assistant Examiner*—Daniel M. Sullivan
(74) *Attorney, Agent, or Firm*—Alice O. Martin; Barnes & Thornburg

(57) ABSTRACT

A novel group of gastrokines called Gastric Antrum Mucosal Protein is characterized. A member of the group is designated AMP-18. AMP-18 genomic DNA, cDNA and the AMP-18 protein are sequenced for human, mouse and pig. The AMP-18 protein and active peptides derived from it are cellular growth factors. Surprisingly, peptides capable of inhibiting the effects of the complete protein, are also derived from the AMP-18 protein. Control of mammalian gastro-intestinal tissues growth and repair is facilitated by the use of the proteins, making the proteins candidates for therapies.

10 Claims, 24 Drawing Sheets

OTHER PUBLICATIONS

Lieske, J.C., et al. (1997) "Adhesion of Hydroxyapatite Crystals to Aniononic Sites on the Surface of Renal Epithelial Cells." *Am. J. Physiol.* F224–F233.

Mansour, S., et al. (1988) "Disruption of the Proto–Oncogene int–2 in Mouse Embryo–Derived Stem Cells: A General Strategy for Trageting Mutations to Non–Selectable Genes." *Nature* 336–348–352.

Moore, K.S., et al. (1991) "Antimicrobial Peptides in the Stomach of *Xenpus laevis*." *J. Biol. Chem.* 266 (2a);19851–19857.

Nguyen, J.T., et al. (1998) "Exploting the Basis of Proline Recognition by SH3 and WW Domains: Design of N–Substituted Inhibitors." *Science* 282:2088–2092.

Nomura, A., et al. (1991) "*Helicobacter Pylori* Infection and Gastric Carcinoma Among Japanese Americans in Hawaii." *N. Engl. J. Med.* 325 (16):1132–1136.

Nusrat, A., et al. (1992) "Intestinal Epithelial Restitution." *J. Clin. Invest.* 89:1501–1511.

Park, C.B., et al. (1997) "A Novel Antimicrobial Peptide From the Loach, *Misgurnus anguillicaudatus*." *FEBS Lett.* 411:173–178.

Parsonnet, J., et al. (1991) "*Helicobacter Pylori* Infection of the Risk of Gastric Carcinoma." *N. Engl. J. Med.* 325 (16):1127–1131.

Podolsky, D.K. (1997) Healing the Epithelium: Solving the Problem from Two Sides. *J. Gastroenterol.* 32:122–126.

Powell, C.T. (1987) "Characterization of a Novel Messenger RNA and Immunochemical Detection of its Protein from Porcine Gastric Mucosa." *Ph.D. Dissertation;* The University of Chicago.

Quaroni, A., et al. (1979) "Epithelioid Cell Cultures From Rat Small Intestine." *J. Cell Biol.* 80:248–265.

Romanos, M.A. et al. (1992) "Foreign Gene Expression in Yeast: a Review" *Yeast* 8:423–488.

Rotimi, V.O., et al. (1990) "Acidity and Intestinal Bacteria: an In–Vitro Assessment of the Bactericidal Activity of Hydrochloric Acid on Intestinal Pathogens." *Afr. J. Med. med. Sci.* 19:275–280.

Sands, B.E. and Podolsky, D.K. (1996) "The Trefoil Peptide Family." *Ann. Rev. Physiol.* 58:253–273.

Schlessinger, J. and Ullrich, A. (1992) "Growth Factor Signaling by Receptor Tyrosine Kinases." *Neuron* 9:383–391.

Sears. I.B., et al. (1998) "A Versatile Set of Vectors for Constitutive and Regulated Gene Expression in *Pichia pastoris*." *Yeast* 14: 783–790.

Segarini, P.R., et al. (1987) "Membrane Binding Characteristics of Two Forms of Transforming Growth Factor–$\beta$" *J. Biol. Chem.* 262 (30):14655–14662.

Smith, D.B. and Johnson, K.S., (1988) "Single–Step Purification of Polypeptides Expressed in *Escherichia Coli* as fusions with Glutathione transferase." *Gene* 67:31–40.

Toback, F.G. (1980) "Induction of Growth in Kidney Epithelial Cells in Culture by $Na^+$." *Proc. Nat. Acad. Sci.* 77 (11):6654–6656.

Yarden, Y. and Ullrich, A. (1988) "Molecular Analysis of Signal Transduction by Growth Factors." *Biochemistry* 27:3113–3119.

Yoo, O.J. et al. (1982) "Molecular Cloning and Nucleotide Sequence of Full–Length cDNA Coding for Porcine Gastrin." *Proc. Natl. Acad. Sci. USA* 79:1049–1053.

Yoshikawa, Y., et al. (2000) "Isolation of Two Novel Genes, Down–regulated in Gastric Cancer." *Jap. J, Cancer Res.* 91:459–463.

* cited by examiner

```
   1  AGCTTTATAA CCATGTGATC CCATCTTATG GTTTCAATCC ATGCACAGGA
  51  GGAAAATTGT GGGCACGAAG TTTCCAAAGG GAAAATTTAT AGATTGGTAG
 101  TTAATGAAAT ACAGTTTTCC TCCTTGGCAA ATTTAATTTA CTAGCTTCAC
 151  TGTATAGGAA AAAGCAGGAA AAAAATTAAA ACCAACTCAC CTCCAAACCT
 201  GTTTTGAGCT TTTACTTGTC TGCCCAATTG ATAGTTTCTA CTCTCTGCTT
 251  TTGATGAAAA TATTTTTTAT TATTTTAATG TAACTTCTGA AAACTAAATT
 301  ATCTAGAAGC AAATAAAAAG ATATTGCTTT TATAGTTCCC AGAAGGAAAA
 351  AACAAACACT AGGAAAGTTC TATCTATCAG ATGGGGAGA TGTGATGGAG
 401  GCAGTGATAT TTGAGCTGAG CCTTGAACAA TGAACAGGAG TCTACCAAGC
 451  GAGAGGCTAG CGGGTGGCCC TCAAGATAAA ACAACAGCAT GTACAAAGGC
 501  ATGGAGACAT ACACATCTTG ACTCTTCCAG GAATGGTGGG AACGCTGGTG
 551  GAGCTAGAAT GTAGGTACAT AGCATAAAGT GGCAGACGGG AAGCCTTTGG
 601  AAATCTTATT ACATAGGACC CTGGATGCCA TTCCAATGAC TTTGAATTTT
 651  CTGTAGGCTG CCAGCGAAAT TTCCAAGCGT GATAGAGTCA TGTCTATCTA
 701  TGCACTTCAG AAAGACAACC TCAGGGTTAA TGAAGAAAAT GCATTGGAAT
 751  ATAAGAAACT GGTGACCAGA GTGATCAATT GCATGACTGT TGTGAAAGTC
 801  CAGGTGAGGG GAGCTGTGGG CAAGGTCAGA GTTGAGAGGC ATTTCAGAGA
 851  TAAAATGACA GTAACTAAGT AGATGTCAGG CTGAGAAGAA AGGGCTGTAC
 901  CAGATATATG GTGCTATCAT TAAGTGAGCT CAACATTGCA GAAAAGGGGT
 951  AGGTTTGGTG GGAGTTGCTC ACAAAACATG TTTAGTCTAA GCAAAACCAT
1001  TGCCATGGGC TCAGATAAAA GTTAAGAAGT GGAAACCATT CCTACATTCC
1051  TATAGGAGCT GCTATCTGGA AGGCCTAGTA TACACGTGGC TTTTCAGCTG
1101  TGATTTTGTT TGATTTTAGG GATTATTCTT TTTCTGAATC TGAGCAATGT
```

FIG. 1A

```
1151  TAGCGTGTAA AATACTCACA CCCACAGCTT TGACTGGGTG AGAAGTTATC

1201  ATAAATCATA TTGAGTTTGT TGTGATACCT TCAGCTTCAA CAAGTGATGA

1251  GTCAGGTCAA CTCCATGTGA AAGTTCCTTG CTAAGCATGC AGATATTCTG

1301  AAAGGTTTCC TGGTACACTG GCTCATGGCA CAGATAGGAG AAATTGAGGA

1351  AGGTAAGTCT TTGACCCCAC CTGATAACAC CTAGTTTGAG TCAACCTGGT

1401  TAAGTACAAA TATGAGAAGG CTTCTCATTC AGGTCCATGC TTGCCTACTC

1451  CTCTGTCCAC TGCTTTCGTG AAGACAAGAT GAAGTTCACA GTGAGTAGAT

1501  TTTTCCTTTT GAATTTACCA CCAAATGATT GGAGACTGTC AATATTCTGA

1551  GATTTAGGAG GTTTGCTTCT TATGGCCCCA TCATGGAAAG TTTGTTTTAA

1601  AAAAATTCTC TCTTCAAACA CATGGACACA GAGAGGGGAA CAACACACAC

1651  CAGGTCCTGT TGGGGGGTGG AGAGTGAGGG GAGGGAACTT AGAGGACAGG

1701  TCAATAGGGG CAGCAAACCA CCATGGCACA CATATACCTA TGTAACAAAC

1751  CTGCACGTTC TGCACATGTA TCCCTTTTTT TTAGAAGAAG AAATAATGAA

1801  AAAAAACCTT TTTTCTATTT ATATAATCAT GGCATTTATA AGCATCTCTA

1851  TAGAGAAGGA TAATTGTGCT GAGATTAGAC AGCTGTCTGA GCACCTCACA

1901  CTGACCTATT TTTAACAAAA TGACTTTCCA CATCACCTGA TTTCGGCTCC

1951  ATGCRGGGTA AGCAGTTCCT AAGCCCTAGA AAGTGCCGAT CATCCCTCAT

2001  TCTTGAATTC CTCCTTTTAT TTACCAAAAT TCCTGAGCAT GTTCAGGAAA

2051  GATGAAAAGC TTATTATCAA AATAAGTGGC TGAGATAGAC TTCTTGTCAC

2101  ATTTGTTACA GTAAAATGGG TCTCCAAGAA AGAAAGATTT GCCTTGGGCT

2151  CTAGCATGGC CATTTATTTA AGAAAGCATC TGAAACATGA AGCTACCACA

2201  GCATCTCTCC TGTGGTTCCA GACGGAAGCC TGAGAGTCTA GGAGGAGGTG

2251  GACCGAGAAA CCCTGCCAAA GTAACTAGTA GTGCCGGGTT TCTCACAACA
```

FIG. 1B

2301 CGATGCAAAG GGGCTAGAAT CAGATGACTA TTTTCATGTT TCAACATACT

2351 ACACACTGGA AAACGTTACG GCAGACTCTA CTTTATAATG GGGCTGCAAA

2401 TGTAAAATGA CTACTAGAAC TAGGTCCTCT TAATAGCAGC AAAGTTTAAA

2451 AGGGTCAGAG GGAGCTCCAG ACACAGGTTA GATTTGATTT CTCTCCTAGT

2501 TCTGCTGTGA CAAGAGGTA TAAGTTTGGC CAACTCACTT AACCCCTGAA

2551 GCTCAGTTAC CTTATCTGTA AAATGATTGC ATTGTACTAG GTGTTCTCTA

2601 AAATTTCTTC TACCTCTGAC TTTTTAGGAG ACTAATTTTT AACTCCTTTT

2651 TAAGCTATTG GGAGAAAAAT TTAATTTTTT TTCAAAAGTT ACCTTGAATC

2701 TCTAGAGCAG TTCTCAAAAC TATTTGTCC CAGGCAAAGG AAATGAGACT

2751 AGGTACCCAG AATGAGGCAC CCTGCATAAA GCTCTGTGCT CTGAAAACCA

2801 ATGTCAGGGA CCCTGTGATA AATAATTAAA CCAAGTATCC TGGGACACTG

2851 CTAGTGACAT CGCCTCTGCT GATCACTCTT GCCAGCGAGA CACTCTATAC

2901 TTGCTTTCTC ATCATTGGCA TCCAAACTGC CTACTAATCC ATTGCTTTGG

2951 AAAGTTTTTT TTAATAAAAA GATTATTTCT ATTAGGAGGA AAACATCCCA

3001 TGTTAAATAG GAAAATTAAC TGAAATCATT TTCAGATGTG ATTTTTAGCA

3051 CTTATAGCCA TTTCAAACCA TGGTATTCAT TTATACTATG CTATTTATTG

3101 TAAAACTTCT TTTTTTTTCC AAGGAAAATA AGATAGTTTG CTTTATTTTA

3151 AAACAGTAAC TTTCTTATAT TGGGGCACTG ACCAAAATTC AATACTGGTA

3201 CAAATATGTT ACCTAGGGGG TCAAAATATG TGCCAGGTGA ATTTTCTGAA

3251 TTTCTCTAAA GAGAGAATTT TAAACCTTAT AAAACAATTA GAAACAAGTG

3301 AGTGAGAGGT GAGCATCAAC AACCTGTGTA ACATAAGCCA CAGTACAAAT

3351 TTAAGCTGAA TAACCAAGCC ATGTCAGTTA TCCCAAATCA TTTTTGTTAA

3401 TATTTAGGAG GATACACATA TTTTCAATAA CTTAAAAGTG AATCTTTACT

3451 CCTATCTCTT AATACTCGAA GAAGTATAAC TTTCTTCTTT TACTAGATTT

FIG. 1C

```
3501  AAATAATCCA AATATCTACT CAAGGTAGGA TGCTGTCATT AACTATAGCT

3551  GAGTTTATCC AAAATAGAAA AATCATGAAG ATTTATAAAG CATTTTAAAA

3601  ATAATCATTT ATAGCAAGTC CTTGAAAGCT CTAAATAAGA AAGGCAGTTC

3651  TCTACTTTCT AATAACACCT ATGGTTTATA TTACATAATA TAATTCAACA

3701  AAACAGCATT CTGACCAATG ATAATTTATA GGAAATTCAT TTGCCAAGTA

3751  TATGTTTTAT TATAAAGTTA ATATTTGAC CAATCTTAAA AATTTTTAAA

3801  CTCTATTCTG ACATTCCAG AAGTATTATC TTAGCAAGTC ATCTTTATGA

3851  TACCACTTAT TAAACTGAAG AGAAACAAGA TGGTACATTC TGGGTTTTAC

3901  TTTAAAAGGG ATTTGATTCA ATAATTTGAT TTATCACTAC TTGAAAATTA

3951  CATTTCTTC CTCAGACTGG ATGGCAATGA GATGAAAGCA GCTTTCCTGG

4001  CTCTCAACTT CCCTTCTTCA TCAATTTTTC CAGCGTTTCA TAAGGCCTAC

4051  ACTAAAAATT CTAAAACTAT ATATCACATT AATATAATTA CTTATAATTA

4101  ATCAGCAATT TCACATTATC GTTAAAACCT TTATGGTTAA AAAATGCAAG

4151  GTAAGAGAAG AAAAAAACAC ATTGAACTAG AACTGAACAC ATTGGTAAAA

4201  TTAGTGAATA CTTTTCATAA GCTTGGATAG AGGAAGAAAG AAGACATCAT

4251  TTTGCCATGT AACAGGAGAC CAATGTTATT TGTGATTTCA GATTGTCTTT

4301  GCTGGACTTC TTGGAGTCTT TCTAGCTCCT GCCCTAGCTA ACTATGTAAG

4351  TCTCACCTTT TCAAGTTTGC TACCAAAATG CATTTGCAAG GAAATGTGAT

4401  ATTAAATCAC TCTCAATCTC TTATAAACTT CAGAATATCA ACGTCAATGA

4451  TGACAACAAC AATGCTGGAA GTGGGCAGCA GTCAGTGAGT GTCAACAATG

4501  AACACAATGT GGCCAATGTT GACAATAACA ACGGATGGGA CTCCTGGAAT

4551  TCCATCTGGG ATTATGGAAA TGTAGGTAGT CAACGTGCAA TTTTCACTTT

4601  ATTGTTTAAA AATACGACTT CTTTTTAACA AAAAATGTGC ATGTTAACCA

4651  TAAAGAAATT AAAAATAAAT TCTAATTACA CATAGCATAC AGTTATAAGT
```

FIG. 1D

```
4701  AAAGGTGACC ATTTTGCTCA TCCGATTTTG TTCCCTAGAG ATAACTACTG

4751  TTAATAAGTG TTGCATGATC AGTTAAAATT CAAACCAACA AACACTATGT

4801  TCAAGGGATT GTGGGTATAT ACAACAAATA TGAACATCCT TTTGCCTTGC

4851  CTGCAGATAC CCTCAATAAT GCTGAAAGAC TTATACAACA TTACTGCTTC

4901  CAAAGCTTAG ACTATCTCAC TTTGTTTTCA AGGAGGTTT TACGACCTTC

4951  TAAAGAGATT GAAATTGACA TTTCACCTAA AACTCGGGAA ATGTAAATGA

5001  CAATATTAAT TGGTAAGAGA GGAAAGAAGA AAGAAAGAAG GAAGGAAAGA

5051  AAGAAAGAAG GAAGGAAGGA AAGAAAGAAA GAAAGAAAGA AAGAGAGAGA

5101  AAGAAAGAAA AAGAAAAAAG AGAGAAAGAG AGAAGGAAAG AAAGAGAGAA

5151  GGAAAGGAAA AGAGAAGCAA AGAAAGAGAG GAGCAAAGAA AGGAACACTT

5201  AGCACTAGTT GGGAGACCCA ACTCTGGAAT TATCAGCTAT ATATTTAACA

5251  AACGTTATAC TTTTAAATAG CAAACTCTTT ATTGTTTCAA TTTTATCTGG

5301  TCAATTGGAA AAATAATTTT TGTCTTATCT GTCTCCTTGA AATGTGAGGA

5351  TCAAAGGAGA CTAAAACATG ATAGCTTTTA AAGTCTATTT CAGTAAAACA

5401  GACTTATATA GAGGGGTTTT TATCATGCTG GAACCTGGAA ATAAAGCAAA

5451  CCAGTTAGAT GCTCAGTCTC TGCCCTCACA GAATTGCAGT CTGTCCCCAC

5501  AAATGTCAGC AATAGATATG ATTGCCAAGC AGTGCCCCAT CCAGTGCTCT

5551  TATCCCAGCT CATCACGATC TTGGAGTTCC CATTTCTCTC TGCAGGTGGA

5601  ACTGACCTCT GATAAGAAAA GCTCCTCGGA GAACACATGC CTCACTATTT

5651  GCCATCTACT TTAACAGGGC TTTGCTGCAA CCAGACTCTT TCAAAAGAAG

5701  ACATGCATTG TGCACAAAAT GAACAAGGAA GTCATGCCCT CCATTCAATC

5751  CCTTGATGCA CTGGTCAAGG AAAAGAAGGT AAAAATAAAA GGCTTTTTAT

5801  TTTTGGTGAG GGAGAGGTT TTACATCCTT CAGTAAATAA CGAGAAGATC

5851  ACAGTCATTC CCTCTTGACT ACAGTATGTT GTAGTGTGCA GCACAAAGGG
```

FIG. 1E

```
5901  GGAAGTTATT GGTGATTGCC TGAGGGAAGG CAACTTCTGC CACATCAAAT

5951  GCTGTGGCTC ACACCTACCT CTACAACCGC TGAGCAAAGC ACTTGAAACC

6001  TTGACTGTTA GAGGAGCAAA GCTCTGGTCA CACCAATAGG AGCCTCAGTA

6051  CTTTGCCAAG GACATTTTTC TGCAAGAGTT AGTTAGGGTT ATTAGATTTA

6101  GCAAATGAAA ATAGAAGATA TCCAGTTAGG TTTGAATTTT AGGTAAGCAG

6151  CAGGTCTTTT TAGTATAATA TATCCTATGC AATATTTGGG ATATACTAAA

6201  AAAAGATCCA TTGTTATCTG AAATTCAAAT GTAACTGGGT ATTGTATATT

6251  TTGTCTGGCC ATACTAATCC AGGTGAGTGG AAAGAAGAGA TCCATAATGT

6301  TTTAAAATAT TTGCCTGAGT TCATATTCCT ATAACTGATA AATGAGTACC

6351  TTTCATTGAC AAGGTAGAGA AAATAAATAA ACTGCATTCT CAGAAGATGA

6401  TTATTACATA GTCTAATCCA AGGAATCTAT GATGACCAAA TGAGGTCCAA

6451  GTTGCAGAAT AAATTAAGCC TCAGACTTCT GTGTTTATGA GAAGCTGAGG

6501  TTTCAAACCA GGTAAATCCC TTAGGACACT TAGAAATGCT AAGATATACA

6551  GAATAAGCTA GAAATGGCTC TTCTTCATCT TGATTATGGA AAAATTTAGC

6601  TGAGCAACAC TCACTGTTGG CCTCGTATAC CCCTCAAGTC AACAAACCAC

6651  TGGGCTTGGC ATTCATTCTC TCCCATTCTT CCTTTCTACC TCTCTTTTCC

6701  ACACTCAGCT TCAGGGTAAG GGACCAGGAG GACCACCTCC CAAGGGCCTG

6751  ATGTACTCAG TCAACCCAAA CAAAGTCGAT GACCTGAGCA AGTTCGGAAA

6801  AAACATTGCA ACATGTGTC GTGGGATTCC AACATACATG GCTGAGGAGA

6851  TGCAAGGTGA GTAGCATCCC TACTGTGCAC CCCAAGTTAG TGCTGGTGGG

6901  ATTGTCAGAC TATCCTCGCG CGTGTCCATA GTGGGCACCA GTGATGCAGG

6951  GATGGTCATC AAGGCCAACA TTTGTGCAGT GCTTGCTCTG TGCCAGGTAC

7001  TGTTCTATGT GCTTTAAGTG TGTTAACTCG GTTCTTCACA GCAATCTTAT

7051  AGGTTCTATT TTAATCCTAC TTTATGGATG AGGAAACTGA GGTACAGAGA
```

FIG. 1F

```
7101  GGTCACAAAA TCCTTGCCTG GGTCAATTCC AAGCATTTTG GCTGTGGATT

7151  CTGTGCTCTT AAATATTATG AACACTGCC TTTTAAGTGT GAATCAAGAG

7201  TAGACTCAAG TCATATTCAA AGAATGCAT GAATGGCTAA ATGAAAGAAG

7251  AATGCTAATA GAATCTATTA ACTTTCTATA GCTCAGACAA TCACTTAATT

7301  TCTGGACATT CAAAGAACAG CTGCACACAA ACAAAGTGTC TACCTAGGGA

7351  CCTAACTTAA TGGCAATTTT CCAGATCTCT GAATTGATTG ATTTCATCAC

7401  AACAAGTAGA TAAACCTTGA CATTAGCACA TAGCTAGTTT GGAAACCCCT

7451  ACTCCCCCAA TCCCCTCCAA GAAAAGAGTC CTTAAATAGA CATTAATATA

7501  GGCTTCTTCT TTTCTCTTTA TTAGAGGCAA GCCTGTTTTT TTACTCAGGA

7551  ACGTGCTACA CGACCAGTGT ACTATGGATT GTGGACATTT CCTTCTGTGG

7601  AGACACGGTG GAGAACTAAA CAATTTTTTA AAGCCACTAT GGATTTAGTC

7651  ATCTGAATAT GCTGTGCAGA AAAAATATGG GCTCCAGTGG TTTTTACCAT

7701  GTCATTCTGA AATTTTTCTC TACTAGTTAT GTTTGATTTC TTTAAGTTTC

7751  AATAAAATCA TTTAGCATTG AATTCAGTGT ATACTCACAT TTCTTACAAT

7801  TTCTTATGAC TTGGAATGCA CAGGATCAAA AATGCAATGT GGTGGTGGCA

7851  AGTTGTTGAA GTGCATTAGA CTCAACTGCT AGCCTATATT CAAGACCTGT

7901  CTCCTGTAAA GAACCCCTTC AGGTGCTTCA GACACCACTA ACCACAACCC

7951  TGGGAATGGT TCCAATACTC TCCTACTCCT CTGTCCACTG CTTAA
```

FIG. 1G

```
  1 CATGCTTGCC TACTCCTCTG TCCACTGCTT TCGTGAAGAC AAGATGAAGT
 51 TCACAATTGT CTTTGCTGGA CTTCTTGGAG TCTTTCTAGC TCCTGCCCTA
101 GCTAACTATA ATATCAACGT CAATGATGAC AACAACAATG CTGGAAGTGG
151 GCAGCAGTCA GTGAGTGTCA ACAATGAACA CAATGTGGCC AATGTTGACA
201 ATAACAACGG ATGGGACTCC TGGAATTCCA TCTGGGATTA TGGAAATGGC
251 TTTGCTGCAA CCAGACTCTT TCAAAAGAAG ACATGCATTG TGCACAAAAT
301 GAACAAGGAA GTCATGCCCT CCATTCAATC CCTTGATGCA CTGGTCAAGG
351 AAAAGAAGCT TCAGGGTAAG GGACCAGGAG GACCACCTCC CAAGGGCCTG
401 ATGTACTCAG TCAACCCAAA CAAAGTCGAT GACCTGAGCA AGTTCGGAAA
451 AAACATTGCA ACATGTGTC GTGGGATTCC AACATACATG GCTGAGGAGA
501 TGCAAGAGGC AAGCCTGTTT TTTTACTCAG GAACGTGCTA CACGACCAGT
551 GTACTATGGA TTGTGGACAT TTCCTTCTGT GGAGACACGG TGGAGAACTA
601 AACAATTTTT TAAAGCCACT ATGGATTTAG TCATCTGAAT ATGCTGTGCA
651 GAAAAAATAT GGGCTCCAGT GGTTTTTACC ATGTCATTCT GAAATTTTTC
701 TCTACTAGTT ATGTTTGATT CTTTAAGTT TCAATAAAAT CATTTAGCAT
751 TG
```

FIG. 2

| | | |
|---|---|---|
| 1 | MKFTIVFAGLLGVFLAPALANYNIDVNDDNNNAGSGQQSVSVNNEHNVAN | 50 |
| 51 | VDNNNGWDSWNSIWDYGNGFAATRLFQKKTCIVHKMKKEVMPSIQSLDAL | 100 |
| 101 | VKEKKLQGKGPGGPPPKGLMYSVNPNKVDDLSKFGKNIANMCRGIPTYMA | 150 |
| 151 | EEMQEASLFFYSGTCYTTSVLWIVDISFCGDTVEN | 185 |

FIG. 3

```
   1 GAATTCAAAC AGCAGGCCAT CTTTCACCAG CACTATCCGA ATCTAGCCAT
  51 ACCAGCATTC TAGAAGAGAT GCAGGCAGTG AGCTAAGCAT CAGACCCCTG
 101 CAGCCCTGTA AGCTCCAGAC CATGGAGAAG AGGAAGGTTG TGGGTTCAAG
 151 GAGCTTTTCA GAGTGGAAAT CTGTGGATCA GTGATTTATA AAACACAGTT
 201 TCCCCCTTTA TTAGATTTGA ACCACCAGCT TCAGTTGTAG AAGAGAACAG
 251 GTTAAAAAAT AATAAGTGTC AGTCAGTTCT CCTTCAAAAC TATTTTAAAC
 301 GTTTACTTAT TTTGCCAAGT GACAGTCTCT GCTTCCTCTC CTAGGAGAAG
 351 TCTTCCCTTA TTTTAATATA ATATTTGAAA GTTTTCATTA TCTAGAGCAG
 401 TGGTTCTCAT CCTGTGGGCC ATGAGCCCTT TGGGGGGGTT GAACGACCCT
 451 TTCACAGGGG TCACATATCA GATATCCTGC ATCTTAGCTA TTTACATTAT
 501 GATTCATAAC AGTAGCAAAA TTAGTTAGGA AGTAGGAACA AAATAACGTT
 551 ATGGTTGTGG TCACCACTAT GTTAGAGGGT CCGCAGCATT CAGAGGGTTG
 601 AGAACTGTTG TTCTAGAGGC AAATAAGAAG ACAGAGTTCC TTGATAGGGC
 651 CCAGAGGCAG TGAAAGAAGT TTCCACGTAG AAAGTGAAGA AGGTCTGGTG
 701 TCCGAAGCAG TGAGGAACTT AAAAAAAGAA AACCAAAAAC ATTGCCAACT
 751 AACAGTCCAG GAGAAGAGCG GGGCATGAAA GGCTGAGTTC CCATGGGATG
 801 CCTTGAATGG AATCAGAGTG TGGGAAAATT GGTGTGGCTG AAGGCAGGT
 851 GCCGGGCATC TCAGACGCTG GTAGCTGGGG AAACAGGAAA CCCCTTTAGG
 901 ATCCCAAGAT GCCATTCCAA TGAGCTTGAG ATTTTTCTCA TGGACTGCCA
 951 GTGAATGTTT CTACGCTCCG GAAATTAATG TTTACTTATT TTCCATATTC
1001 TAGGGGAGAA CCCTGGGAAA AATGGAGGAC ATTCATTGAA ATATCTGAGT
1051 CCTGGGATAA GGCAGGCTTG GTCCTACAAC TCTGGTAAAA GTCCATCAGG
1101 AAGTGCCTTG ACCAAGGCTG GAGTGGAGAG CTGTTGGTGA GATGTAAGGG
```

FIG. 4A

```
1151  CAAGGTTTAG TTGCTAGATA TGTAGATGGC AAGATGGTGC TGCCAACAGC

1201  CCCCAGAGCT CTAACCCACT GAGAAACCCA GGAATGAATG ATGGGAGATG

1251  GCTTTGGTGC CAGCTGCTAG TGACATGGCT GGAAAGCTGC ACTGGCTTCG

1301  AGGCCAGACA ATTCCTCAAG GAAACATCTG GCCAGGGTGC AAGGGCCAGT

1351  TTCCTTCCTT GGAGTTCCTT TCACAGCTAA GAACATCATC CCCCAACCAC

1401  TGGTTTTGTT AAAAAGTTTT CAGTATGACT TGAGCATGGT CAAGAAGCAT

1451  AGAGAGGGGG AAATAAGGGT GGAAGGAGCT GGAGAAAGCT TACAATAGGA

1501  CTGGGTAAAG GGAAGGAGAA GAAACCATTC CCGCATTCCC ATAGGAGCCA

1551  GTACCAGGAA GGGCAGGTGT ACACACAGAT CTCATCTAAG GCCATGTTTG

1601  GTTTAGGGAT TACTCTTCTC CCGAATCTGA GCAGCAGCAA TACGTAAAAT

1651  ACCCACACCC ATGGCTTCCA TATTCCAGAA CTTATCACAA ACCGTGTAGA

1701  GTTTACTGAG ATACCTTCGT CAGAGGATGA GTCAGAGGCC TCCTGCCTAA

1751  GGGCCCTACT GAGCAGGCAG CTAAAGGCTT CCGGGCCTCT GCAGCTCCAC

1801  AGATACAGGA GAGGGAAGCA GATAAGCCGT GGACTCCACC TGAGCACACC

1851  TAGCTTGAGC AAAGCTGGTC AGGTACAAAT AGCAGAGGGC TGAATGTCTG

1901  TGAGCACGCC GCCTGATCCT CTGCTCCACC ACACTCCTGC CGCCATGAAG

1951  CTCACAGTAA GTCAGATCTT CTTTTCAATG CAGCACCATA CAACATTAAT

2001  AGTCAGGGGT GAGGGGGTCT GACTCTTACG GCACTGTTAC CATAGTGGAA

2051  ATATTCTCCT TTCTTTTCAT GGAATCATGG TGTTTACAAG CATGTCCATA

2101  GAGAAGAAGA ATTGCCCCGG AAGAGCCTGT CACAGGCTGA ATACTGTAGA

2151  ATTGTCTTTC ACACCATCTG TTCCAAGGTT CTACTTAAGA CGAGCAGTCT

2201  CTGGGCTCCA GAAAGAGTCT TTCTTAGCCT TGATCTCTTT CTTATTTCTG

2251  ATTTCTCCTT TCTTATCCAT GATTTCCACT TTTACCAGTT CTGGGCATGT
```

FIG. 4B

```
2301   TCCGGTCAGA CTGGAAGATC ACTGTTGTCA AAACTAGTCT TCAACACTCT

2351   TGGCTGTTAA CATGAAAACA ACGGTCCTTG GGCCCTGTGC AAGCATTTCT

2401   TGGAGAAAGT CTCTGGGGAT GAAGCTATCT CAGTTTCCCC ACTGAAGTCC

2451   TAGGATACAG AGGCTCAAAC AGAGTGCACA TATTCAATTT CAGCATACTC

2501   TATTGGCGCT GCTTTATGAA TCATATGAAT TTATGGAATT GGAAATGTAA

2551   ACTATGACCA AGAAGCGTCC ACCTCAGAAC AGGTTGGGTG GGGAACTCCA

2601   AGCACAGGCC AGAGGGCTGC GTTTCTTTC TAGTTCTGTC TAGAGGAGTG

2651   GTTCTCGACC TTCCTAATGC TGTGACCCTT AATACAGTT CCTCACGTTG

2701   TCGTGACTCC CAGCCATAAA ATTACTTTCA TTGCTACTGC ATAACTGTAA

2751   TTTTGCTACC ATTATGAGTT GTAATGTAAA TATCTGATAT GCAAGATACC

2801   AGATAACCTA AGAAACGGTT GTTTGACCTT TAAAGGGGTC ACAACCCACA

2851   GGTGGAGAAC TACTGGTCTA GGGTCCTTTA CAGTCCTTTA GCTGCCTCAT

2901   TTACAGGAGA TAACATCATG CTCAAAAACT CCCTCCACAT TTGGCTTTTT

2951   GGGTTGTTTT GTTTTGTTTT TCAAGACAGG GTTTCTCTGT GTAGCCCTGG

3001   CTGTCCTGGA ACTCACCTTT GTAGACCAGG CTGGCCTCGA ACTCAGAAAT

3051   CCGCCTGCTT CTGCCTCCTG AGCGCTGGGA TTAAAGGCGT GCGCCACCAT

3101   GTCTGGCTCA CATCTGGCTT TTTAAGAGAC CGATTTTAAC TTCTTGCATT

3151   GAAAATAAAT ATAGTAGAAA TGCTTAACCT ACTAAGACAA TAAAAACAGG

3201   ATTCCTTCTG CTAGGAAGAA CACGTTCCAG ACTAAGGAAA AAAACCTTTT

3251   CAGGGCTTTC ATTACACTGT GCCATGCACT AATTTTATGT TTTCTTCATC

3301   AGTTTTCAGT GTCTGAAATT CAGTGTCAAA ATTCTAAGAC TACATATGAA
```

FIG. 4C

```
3351  TATCATTACA GTAACTCAGC AATTCTATGT TACCAGTAAG TTTTTCTGTA

3401  GTTTAAAAAA AAGGTGGAAG AAGAAAGCAC AGATAGTTTA GCACATGGGT

3451  AAAATCAGTA ACTATTTCTG ATGAGCTTGG TGAAGATGCT GTAAACCATG

3501  CGACCACCAG TCCTGTTCTC TGTGCTTTCA GATGTTCGTC GTGGGTCTGC

3551  TTGGCCTCCT TGCAGCTCCT GGTTTTGCTT ACGTAAGTCT CATTTTCTG

3601  AAGTTCATTG TCAAAACTGC ATTACAGTG AAATGTGATC TTAAGTCACC

3651  CTCTGCTTCT TATGAACATT AGACGGTCAA CATCAATGGT AATGATGGCA

3701  ATGTAGACGG AAGTGGACAG CATTCGGTGA GCATCAATGG TGTGCACAAC

3751  GTGGCCAATA TCGACAACAA TAACGGCTGG GACTCCTGGA ATAGCCTCTG

3801  GGACTATGAA AACGTATGTA ATGGACACAC AGGGTAAAGA TATGGTGTAG

3851  CCACCACCCA TTAAAATTTC TGAGGTGAAT CTAGCTGTT CATGAACATT

3901  AAAAGCTACC AGTAAAAGTG CCCATTCCAC TCAAAACAAT TTTACTTTTT

3951  TGCATATAAT TATTGCTAAT AAGTATTACA CAATAGGTCG AAATTCAAAG

4001  GGATCAATAG TAAGGATAAA AACTATGTAC AAAGACAAAC ACAGCATCCT

4051  TTGGTCTTCC CTGCAGAGAG TCTCCATGAT GTTAAAGGTC CAATGTTTTA

4101  TGGAGGCTGA ATGAAATACG AATGCCTCTG TGATGGAAAA GGCCCAACAT

4151  CTTATGGAGA ATGAGTGAAG TATGAATGCT ATTAGTTGTA AGAGAAGGCG

4201  ATGCAAAGCA ACACTTGGCA CCACCTGCCA ATTACTACTT TCCTATTTAA

4251  ATGTAGTTTA AAAAGCAAAG CCTGTCTTCC CTGCCTCCTG GAAACACTGC

4301  GGATGGAGGT AGACCAAGGT ATGACAGCCT TTAAAAGTTT GTCAGCAAAA

4351  CACTCCCCCA TACACACATA CACACACCCT CCTACTACAC TGGAACTGAA
```

FIG. 4D

```
4401  GCAAAGGCAG TGGGTTAGAT ATATCCACCC TCTAAGAGTT TGCAGGTCAT

4451  CTATATATGA TAGCCAGAGA CACAACTGCA GGACAGCCAG ACTCTGAGCA

4501  CTCTCCCCAG CTCCTTGTAG CTCTGTTTCA GTGGTGACTT GTGACAAGAA

4551  TCCTGGGGAA CCTGTGCCTC ACTGTTCTCT GTCTTCTTTA ATAGAGTTTC

4601  GCTGCCACGA GACTCTTCTC CAAGAAGTCA TGCATTGTGC ACAGAATGAA

4651  CAAGGATGCC ATGCCCTCCC TTCAGGACCT CGATACAATG GTCAAGGAAC

4701  AGAAGGTAAA GTCCTGCCTT CTTCTTTGGA GTGACAGGAA GTCTTACAGT

4751  CTCCAGTACA CAGTGAAGTC ACCCCCATTC CCTCTTTGGT GGAGCATGAC

4801  AGCATGTTTG TCATGATAAA TGCCACAAAC ATGTAAAACT GTTCAGTGTC

4851  TGCCTGAATG GAGGGTGGCT TCCACTGTGT CAGATGCCGT GGCCCACATC

4901  TGCCTCTGCA GGGTCCAGTA AAGCACTGGC TATCTTGAGT GTCAGAGACC

4951  CAAAGGTCTG TACACTTCAG TACAAGCCCT CCATATTTCA AGGGCACACT

5001  CCTACAGTCG TTGGGGTTAT CAGAACTAGC AAACATAGAG ACTGGATTTT

5051  CAGATGAAAA GAAATCCTTT TTAAAGTCTA AGTATGCCTT ATACAATGTT

5101  TGAGATATTC TCAATACTAA AAAAAAAAAA ATTGTTGCTT GCTTGAAAAT

5151  CAAATGTAAC CAAGTGTCCT ATATCCAGTG TCAATCATGG CTGTAGTAGA

5201  TGGGAAGAGG GAGCCCGTGG TTTTCACAGT CAGACGCCTG AGTTATTCTT

5251  CTAAGTGATA AATTGGTTCC TATAACAAGC AAGCCAGTGA ATATAAATAA

5301  GCTCTATCTC AGAAGTTATC CTGTAGTGCT ACCCTAGAAT CTAAGAGAGC

5351  AAAAGTGCTT CAAATTTCAG AATAAGTTTT GCTTGGACT TCTGTTTTTC

5401  TAAACAACTA TAACTTCAAA CCATCTAAGC CTCGTGGGAC ACTTAGAAAT

5451  ACCAAGCCAT TCAAAGCTAG AATTGTTTCT TCACCTTACT TGAAAACAAA
```

FIG. 4E

| | | | | | |
|---|---|---|---|---|---|
| 5501 | ATGACAACCA | AAAATTGTCC | CCACTGCCCT | TGTACATCTT | CAGATCAGTA |
| 5551 | AAGTCCTGGG | CTCAGGGATC | ATTCACTTTC | TTTCTTTCCT | TTCACACTCA |
| 5601 | ACTTCAGGGT | AAAGGGCCTG | GAGGAGCTCC | TCCCAAGGAC | TTGATGTACT |
| 5651 | CCGTCAACCC | TACCAGAGTG | GAGGACCTGA | ATACATTCGG | ACCAAAGATT |
| 5701 | GCTGGCATGT | GCAGGGGCAT | CCCTACCTAT | GTGGCCGAGG | AGATTCCAGG |
| 5751 | TGTGTACCCT | GAGATGCTGT | ATATCCCAAT | GCAGTACTGA | GAGAGCCATC |
| 5801 | AGACACTCTA | AAGTGTGACC | ACAGACGGAC | CAATCATGTG | GATTATCAGA |
| 5851 | GCAAACACTT | GCTTGCTCCT | TGTCAGACAG | TTGTCCATGC | TTCAAAAGTT |
| 5901 | CATTAAAAAA | AATAGTTCAC | AGGCTCCTCA | CAGAAACCTT | AGTAGAATCC |
| 5951 | ACAGCTTCTG | CTCTTAGTCT | TACTTTTTAG | AAACTGAGAC | CCAGAGAAAG |
| 6001 | GTCACAAAAC | TTTTGTCTGG | CTCAGGTTCT | ATGTCTTTAA | CTTTATAGAA |
| 6051 | TACCGTCTTT | CTGGGTGGGT | GGGCTCTAGA | GTAAACTTCA | AGTGAGTTCA |
| 6101 | AGGAAAGCAT | GAGAAGTAGG | GAAGACCAAA | TGAAAGGAGA | ATGCCAATGA |
| 6151 | AATCTATCGA | TTCTATAGCG | CCAATGCTTA | ACTCCTAGGC | GTTCAAAGAA |
| 6201 | TAGTATCCAC | AAGGTGTCAG | CCTAAGATCC | TAATCTAACA | GCAAGTTTTC |
| 6251 | AGATCTCTGA | AGTGAAAAGA | GAAAGCAAGA | GAGGAACAGA | GACAGAAACA |
| 6301 | GTAAGAGACA | GAGAGGCAGA | GACAAAGAGA | CAGGGAGAAT | AGAGAGGGAT |
| 6351 | TAAAATTAAT | ATATAGTTTA | GAAATTACGA | CTCCTCACAG | TCCCTGCAGA |
| 6401 | GTCCTAGGAT | AGGCACTGAT | TTGGACTTCT | TTTCTTCTCA | CTAGGACCAA |
| 6451 | ACCAGCCTTT | GTACTCAAAG | AAGTGCTACA | CAGCTGACAT | ACTCTGGATT |
| 6501 | CTGCGGATGT | CCTTCTGTGG | AACATCAGTG | GAGACATACT | AGAAGTCACA |
| 6551 | GGAAAACAAC | CCGTGGGCTC | TGACCATCGC | AATGCTTGAT | TATGAGAGTG |

FIG. 4F

```
6601   TTCTCTGGGG  GTTGTGATTA  GCTTCTTTAA  GGCTCAATAA  ACCCACGTGG

6651   CAGCACATCC  AGTTTGTAAT  GACATGCCTC  ATGACTTCTA  TGGGAGTCCA

6701   ATGTGGCACC  TGCCAGCCTG  TATTCAGGAC  CTCTCCGCTA  TAAAGCATCC

6751   CTCCAGAGTT  TTCAAATACT  ACAAAGCACA  GCCTGGGTTT  GGGCTCAGAT

6801   AGGCCACTGC  TGCCTGACTA  CATTACAGAC  AAACAAGTTT  TAAAAGAAAG

6851   AAAAAAGAGC  TCAGAGTGGC  TGGAATCAGC  AAGGGTGTTT  TTCCTGCAAG

6901   GAGCCAGAAG  TATCAATAAT  CACCCAAGGA  GGAGACACTG  GGAATGAGAG

6951   ACTAGAACAC  ACGCCTGCAG  ATACGGAGAA  CCTCAGCATT  GCCGCTCTCT

7001   CCCATAACTG  CACACCCCCT  TCTGTAAACT  CTGCTTCTTT  CTTTCACCTG

7051   AAGATGGCCC  TTGCTTTTTT  TTATTATAGG  ACANGATAAC  TAGACCAGAA

7101   AGTCAACCTG  ACTCTCTACA  TTTATATGTC  TTCCCAGNTC  AAGAAATATT

7151   ATTTACTGGT  GAATGGCACT  TCTATATTCC  CTTGGTTCAA  TAAGTCTACA

7201   GGATCCATTC  ATTGACAGGC  CAAGAGTGAG  ATCACATGAT  ACCCAAGCAC

7251   ATGGGTCTTT  CCTTGAAGGA  GAAGGATCCA
```

FIG. 4G

```
  1 ATGTTCGTCGTGGGTCTGCTTGGCCTCCTTGCAGCTCCTGGTTTTGCTTACACGGTCAAC
 61 ATCAATGGTAATGATGGCAATGTAGACGGAAGTGGACAGCATTCGGTGAGCATCAATGGT
121 GTGCACAACGTGGCCAATATCGACAACAATAACGGCTGGGACTCCTGGAATAGCCTCTGG
181 GACTATGAAAACAGTTTCGCTGCCACGAGACTCTTCTCCAAGAAGTCATGCATTGTGCAC
241 AGAATGAACAAGGATGCCATGCCCTCCCTTCAGGACCTCGATACAATGGTCAAGGAACAG
301 AAGGGTAAAGGGCCTGGAGGAGCTCCTCCCAAGGACTTGATGTACTCCGTCAACCCTACC
361 AGAGTGGAGGACCTGAATACATTCGGACCAAAGATTGCTGGCATGTGCAGGGGCATCCCT
441 ACCTATGTGGCCGAGGAGATTCCAGGACCAAACCAGCCTTTGTACTCAAAGAAGTGCTAC
501 ACAGCTGACATACTCTGGATTCTGCGGATGTCCTTTTGTGGAACATCAGTGGAGACATAC
561 TAG
```

FIG. 5

1   MKLTMFVVGL LGLLAAPGFA YTVNINGNDG NVDGSGQQSV SINGVHNVAN

51  IDNNNGWDSW NSLWDYENSF AATRLFSKKS CIVHRMNKDA MPSLQDLDTM

101 VKEQKGKGPG GAPPKDLMYS VNPTRVEDLN TFGPKIAGMC RGIPTYVAEE

151 IPGPNQPLYS KKCYTADILW ILRMSFCGTS VETY

FIG. 6

```
  1  atgcctgact tctcacttca ttgcattggt gaagccaaga tgaagttcac
 51  aattgccttt gctggacttc ttggtgtctt cctgactcct gcccttgctg
101  actatagtat cagtgtcaac gacgacggca acagtggtgg aagtgggcag
151  cagtcagtga gtgtcaacaa tgaacacaac gtggccaacg ttgacaataa
201  caatggatgg aactcctgga atgccctctg ggactataga actggctttg
251  ctgtaaccag actcttcgag aagaagtcat gcattgtgca caaaatgaag
301  aaggaagcca tgccctccct tcaagccctt gatgcgctgg tcaaggaaaa
351  gaagcttcag ggtaagggcc aggggggacc acctcccaag agcctgaggt
401  actcagtcaa ccccaacaga gtcgacaacc tggacaagtt tggaaaatcc
451  atcgttgcca tgtgcaaggg gattccaaca tacatggctg aagagattca
501  aggagcaaac ctgatttcgt actcagaaaa gtgcatcagt gccaatatac
551  tctggattct taacatttcc ttctgtggag gaatagcgga gaactaa
```

FIG. 7

```
1    MKFTIAFAGL  LGVFLTPALA  DYSISVNDDG  NSGGSGQQSV  SVNNEHNVAN

51   VDNNNGWNSW  NALWDYRTGF  AVTRLFEKKS  CIVHKMKKEA  MPSLQALDAL

101  VKEKKLQGKG  PGGPPPKSLR  YSVNPNRVDN  LDKFGKSIVA  MCKGIPTYMA

151  EEIQGANLIS  YSEKCISANI  LWILNISFCG  GIAEN
```

FIG. 8

| | | | |
|---|---|---|---|
| Human | 1 | MKFTIVFAGLLGVFLAPALANYNIDVNDDNNNAGSGQQSVSVNNEHNVAN | 50 |
| Pig | 1 | MKFTIAFAGLLGVFLTPALADYSISVNDDGNSGGSGQQSVSVNNEHNVAN | 50 |
| | 51 | VDNNNGWDSWNSIWDYGNGFAATRLFQKKTCIVHKMKKEVMPSIQSLDAL | 100 |
| | 51 | VDNNNGWNSWNALWSYRTGFAVTRLFRKKSCIVHKMKKEAMPSLQALDAL | 100 |
| | 101 | VKEKKLQGKGPGGPPPKGLMYSVNPNKVDDLSKFGKNIANMCRGIPTYMA | 150 |
| | 101 | VKEKKLQGKGPGGPPPKSLRYSVNPNRVDNLDKFGKSIVAMCKGIPTYMA | 150 |
| | 151 | EEMQEASLFFYSGTCYTTSVLWIVDISFCGDTVEN | 185 |
| | 151 | EEIQGANLISYSEKCISANILWILNISFCGGIAEN | 185 |

FIG. 9

|       | 1          |            |            |            | 50         |
|-------|------------|------------|------------|------------|------------|
| Human | MKFTIVF.AG | LLGVFLAPAL | ANYNIDVN.D | DNNNAGSGQQ | SVSVNNEHNV |
| Pig   | MKFTIAF.AG | LLGVFLTPAL | ADYSISVN.D | DGNSGGSGQQ | SVSVNNEHNV |
| Mouse | MKLTM.FVVG | LLGLLAAPGF | A.YTVNINGN | DGNVDGSGQQ | SVSINGVHNV |

|       | 51         |            |            |            | 100        |
|-------|------------|------------|------------|------------|------------|
| Human | ANVDNNNGWD | SWNSIWDYGN | GFAATRLFQK | KTCIVHKMNK | EVMPSIQSLD |
| Pig   | ANVDNNNGWN | SWNALWDYRT | GFAVTRLFEK | KSCIVHKMKK | EAMPSLQALD |
| Mouse | ANIDNNNGWD | SWNSLWDYEN | SFAATRLFSK | KSCIVHRMNK | DAMPSLQDLD |

|       | 101        |            |            |            | 150        |
|-------|------------|------------|------------|------------|------------|
| Human | ALVKEKKLQG | KGPGGPPPKG | LMYSVNPNKV | DDLSKFGKNI | ANMCRGIPTY |
| Pig   | ALVKEKKLQG | KGPGGPPPKS | LRYSVNPNRV | DNLDKFGKSI | VAMCKGIPTY |
| Mouse | TMVKEQK..G | KGPGGAPPKD | LMYSVNPTRV | EDLNTFGPKI | AGMCRGIPTY |

|       | 151        |            |            | 188        |
|-------|------------|------------|------------|------------|
| Human | MAEEMQEASL | FFYSGTCYTT | SVLWIVDISF | CGDTVEN    |
| Pig   | MAEEIQGANL | ISYSEKCISA | NILWILNISF | CGGIAEN    |
| Mouse | VAEEIPGPNQ | PLYSKKCYTA | DILWILRMSF | CGTSVETY   |

GASTROKINES AND DERIVED PEPTIDES INCLUDING INHIBITORS

The U.S. Government has rights to the invention pursuant to Contract DK21901 between the National Institutes of Health (NIH) and the University of Chicago.

BACKGROUND

A novel group of Gastric Antrum Mucosal Proteins that are gastrokines, is characterized. A member of the gastrokine group is designated AMP-18. AMP-18 genomic DNA, and cDNA molecules are sequenced for human and mouse, and the protein sequences are predicted from the nucleotide sequences. The cDNA molecule for pig AMP-18 is sequenced and confirmed by partial sequencing of the natural protein. The AMP-18 protein and active peptides derived from its sequence are cellular growth factors. Surprisingly, peptides capable of inhibiting the effects of the complete protein, are also derived from the AMP-18 protein sequence. Control of mammalian gastro-intestinal tissues growth and repair is facilitated by the use of the protein or peptides, making the protein and the derived peptides candidates for therapies.

Searches for factors affecting the mammalian gastro-intestinal (GI) tract are motivated by need for diagnostic and therapeutic agents. A protein may remain part of the mucin layer, providing mechanical (e.g., lubricant or gel stabilizer) and chemical (e.g. against stomach acid, perhaps helping to maintain the mucus pH gradient and/or hydrophobic barrier) protection for the underlying tissues. The trefoil peptide family has been suggested to have such general cytoprotectant roles (see Sands and Podolsky, 1996). Alternatively, a cytokine-like activity could help restore damaged epithelia. A suggestion that the trefoil peptides may act in concert with other factors to maintain and repair the epithelium, further underlines the complexity of interactions that take place in the gastrointestinal tract (Podolsky, 1997). The maintenance of the integrity of the GI epithelium is essential to the continued well-being of a mammal, and wound closing after damage normally occurs very rapidly (Lacy, 1988), followed by proliferation and differentiation soon thereafter to reestablish epithelial integrity (Nursat et al., 1992). Thus protection and restitution are two critical features of the healthy gastrointestinal tract, and may be important in the relatively harsh extracellular environment of the stomach.

Searches for GI proteins have met with some success. Complementary DNA (cDNA) sequences to messenger RNAs (mRNA) isolated from human and porcine stomach cells were described in the University of Chicago Ph.D. thesis "Characterization of a novel messenger RNA and immunochemical detection of its protein from porcine gastric mucosa," December 1987, by one of the present inventors working with the other inventors. However, there were several cDNA sequencing errors that led to significant amino acid changes from the AMP-18 protein disclosed herein. The protein itself was isolated and purified only as an aspect of the present invention, and functional analyses were performed to determine utility. Nucleic acid sequences were sought.

SUMMARY OF THE INVENTION

A novel gene product designated Antrum Mucosal Protein 18 ("AMP-18") is a gastrokine. The protein was discovered in cells of the stomach antrum mucosa by analysis of cDNA clones obtained from humans, pigs, and mice. The protein is a member of a group of cellular growth factors or cytokines, more specifically gastrokines. The AMP-18 cDNA sequences predict a protein 185 amino acids in length for both pig and man. The nucleotide sequences also predict a 20-amino acid N-terminal signal sequence for secreted proteins. The cleavage of this N-terminal peptide from the precursor (preAMP-18) was confirmed for the pig protein; this cleavage yields a secreted protein 165 amino acids in length and ca.18,000 Daltons (18 kD) in size. Human and mouse genomic DNA sequences were also obtained and sequenced. A human genomic DNA was isolated in 4 overlapping fragments of sizes 1.6 kb, 3 kb, 3.3 kb and 1.1 kb respectively. The mouse genomic DNA sequence was isolated in a single BAC clone.

The gastrokine designated AMP-18 protein is expressed at high levels in cells of the gastric antrum. The protein is barely detectable in the rest of the stomach or duodenum, and was not found, or was found in low levels, in other body tissues tested. AMP-18 is synthesized in lumenal surface mucosal cells, and is secreted together with mucin granules.

Compositions of AMP-18 isolated from mouse and pig antrum tissue stimulate growth of confluent stomach, intestinal, and kidney epithelial cells in culture; human, monkey, dog and rat cells are also shown to respond. This mitogenic (growth stimulating) effect is inhibited by specific antisera (antibodies) to AMP-18, supporting the conclusion that AMP-18, or its products, e.g. peptides derived from the protein by isolation of segments of the protein or synthesis, is a growth factor. Indeed, certain synthetic peptides whose amino acid sequences represent a central region of the AMP-18 protein also have growth-factor activity. The peptides also speed wound repair in tissue culture assays, indicating a stimulatory effect on cell migration, the process which mediates restitution of stomach mucosal injury. Thus, the protein and its active peptides are motogens. Unexpectedly, peptides derived from sub-domains of the parent molecule can inhibit the mitogenic effect of bioactive synthetic peptides and of the intact, natural protein present in stomach extracts.

There are 3 activities of the gastrokine proteins and peptides of the present invention. The proteins are motogens because they stimulate cells to migrate. They are mitogens because they stimulate cell division. They function as cytoprotective agents because they maintain the integrity of the epithelium (as shown by the protection conferred on electrically resistant epithelial cell layers in tissue culture treated with damaging agents such as oxidants or non-steroidal anti-inflammatory drugs NSAIDs).

The invention relates a group of isolated homologous cellular growth stimulating proteins designated gastrokines, that are produced by gastric epithelial cells and include the amino acid sequence VKEK/QKXXGKGPGGXPPK (SEQ ID NO: 1). An isolated protein of the group has an amino acid sequence as shown in FIG. 7. The protein present in pig gastric epithelia in a processed form lacking the 20 amino acids which constitute a signal peptide sequence, has 165 amino acids and an estimated molecular weight of approximately 18 kD as measured by polyacrylamide gel electophoresis. Signal peptides are cleaved after passage through endoplasmic reticulum (ER). The protein is capable of being secreted. The amino acid sequence shown in FIG. 3 was deduced from a human cDNA sequence. An embodiment of the protein is shown with an amino acid sequence as in FIG. 6, a sequence predicted from mouse RNA and DNA.

A growth stimulating (bioactive) peptide may be derived from a protein of the gastrokine group. Bioactive peptides rather than proteins are preferred for use because they are smaller, consequently the cost of synthesizing them is lower than for an entire protein.

In addition, a modified peptide may be produced by the following method:

(a) eliminating major protease sites in an unmodified peptide amino acid sequence by amino acid substitution or deletion; and/or (b) introducing into the modified amino acid analogs of amino acids in the unmodified peptide.

An aspect of the invention is a synthetic growth stimulating peptide, having a sequence of amino acids from positions 78 to 119 as shown in FIG. 3.

Another peptide has a sequence of amino acids from position 97 to position 117 as shown in FIG. 3.

Another peptide has a sequence of amino acids from position 97 to position 121 as shown in FIG. 3.

Another peptide has a sequence of amino acids from position 104 to position 117 as shown in FIG. 3.

An embodiment of an isolated bioactive peptide has one of the following sequences: LDTMVKEQKGKGPGGAPPKDLMY (SEQ ID NO: 2) or KKLQGKGPGGPPPK (SEQ ID NO: 3). An embodiment of an inhibitor of a protein of the gastrokine group has the amino acid sequence KKTCIVHKMKK (SEQ ID NO: 4) or KKEVMPSIQSLDALVKEKK (SEQ ID NO: 5). (see also Table 1)

The invention also relates a pharmaceutical composition including at least a growth stimulating peptide.

A pharmaceutical composition for the treatment of diseases associated with overgrowth of gastric epithelia, includes an inhibitor of a protein of the group of gastrokines or of a growth stimulating peptide derived from the gastrokine proteins.

A pharmaceutical composition for the treatment of diseases of the colon and small intestine includes at least a growth stimulating peptide of the present invention. Examples of such diseases include ulcerative colitis and Crohn's Disease.

Antibodies to the protein product AMP-18 encoded by the human cDNA expressed in bacteria were produced in rabbits; these antibodies reacted with 18 kD antrum antigens of all mammalian species tested (human, pig, goat, sheep, rat and mouse), providing a useful method to detect gastrokines. An antibody to a protein of the group recognizes an epitope within a peptide of the protein that includes an amino acid sequence from position 78 to position 119 as in FIG. 3.

The invention is also directed to an isolated genomic DNA molecule with the nucleotide sequence of a human as shown in FIG. 1 and an isolated cDNA molecule encoding a human protein, that the nucleotide sequence as shown in FIG. 2.

Another aspect of the invention is an isolated DNA molecule having the genomic sequence found in DNA derived from a mouse, as shown in FIG. 4.

Genomic DNA has value because it includes regulatory elements for gastric expression of genes, consequently, the regulatory elements can be isolated and used to express other gene sequences than gastrokines in gastric tissue.

An aspect of the invention is a mouse with a targeted deletion in a nucleotide sequence in the mouse genome that, when expressed without the deletion, encodes a protein of the group of gastrokines of the present invention.

An aspect of the invention is a method of making a gastrokine protein or a peptide derived from a gastrokine protein. The method includes:

(a) obtaining an isolated cDNA molecule with a sequence such as that shown in FIG. 2;

(b) placing the molecule in a recombinant DNA expression vector;

(c) transfecting a host cell with the recombinant DNA expression vector;

(d) providing environmental conditions allowing the transfected host cell to produce a protein encoded by the cDNA molecule; and (e) purifying the protein from the host cell.

Host cells in which expression has been successful include baculovirus, which allows large amounts of gastrokines to be provided for commercial and research uses. For example, human AMP-18 protein without the signal peptide was produced.

An aspect of the invention is a method to stimulate growth of epithelial cells in the gastrointestinal tract of mammals. The method includes the steps of:

(a) contacting the epithelial cells with a composition comprising a gastrokine protein or a peptide derived from a protein of the group; and (b) providing environmental conditions for stimulating growth of the epithelial cells.

A method to inhibit cellular growth stimulating activity of a protein of the group includes the steps of:

(a) contacting the protein with an inhibitor; and (b) providing environmental conditions suitable for cellular growth stimulating activity of the protein.

The inhibitor may be an antibody directed toward at least one epitope of the protein, e.g. an epitope with an amino acid sequence from position 78 to position 119 of the deduced amino acid sequence in FIG. 3 or an inhibitor peptide such as those in Table 1.

A method of testing the effects of different levels of expression of a protein on mammalian gastrointestinal tract epithelia, includes the steps of:

(a) obtaining a mouse with an inactive or absent gastrokine protein;

(b) determining the effects of a lack of the protein in the mouse;

(c) administering increasing levels of the protein to the mouse; and (d) correlating changes in the gastrointestinal tract epithelia with the levels of the protein in the epithelia.

Kits are contemplated that will use antibodies to gastrokines to measure their levels by quantitative immunology. Levels may be correlated with disease states and treatment effects.

A method to stimulate migration of epithelial cells after injury to the gastrointestinal tract of mammals, includes the steps of:

(a) contacting the epithelial cells with a composition comprising a peptide derived from the protein; and (b) providing environmental conditions allowing migration of the epithelial cells.

A method for cytoprotection of damaged epithelial cells in the gastrointestinal tract of mammals, includes the following steps:

(a) contacting the damaged epithelial cells with a composition including a protein of the gastrokine group or a peptide derived from the protein; and (b) providing environmental conditions allowing repair of the epithelial cells.

The damaged cells may form an ulcer.

BRIEF DESCRIPTION OF THE DRAWINGS

FIGS. 1A–1G is a human genomic nucleotide sequence (SEQ ID NO: 1) of a pre-gastrokine; sequence features were determined from cDNA and PCR of human genomic DNA amph-ge8.seq Length: 7995 predicted promoter: 1405; exon 1:1463–1490; exon 2: 4292–4345; exon 3: 4434–4571; exon 4: 5668–5778; exon 5: 6709–6856; exon 6: 7525–7770; polyA site: 7751.

FIG. 2 is a human cDNA sequence (SEQ ID NO: 12); the DNA clone was obtained by differential expression cloning from human gastric cDNA libraries.

FIG. 3 is a human preAMP-18 protein sequence (SEQ ID NO: 13) predicted from a cDNA clone based on Powell (1987) and revised by the present inventors; N-21 is the expected N-terminus of the mature protein.

FIGS. 4A–4G is a mouse preAMP-18 sequence (SEQ ID NO: 14) determined from RT-PCR of mRNA and PCR of BAC-clones of mouse genomic DNA sequences: predicted promoter: 1874; experimental transcription start site: 1906; translation site: 1945; CDS 1: 1906–1956; CDS 2: 3532–3582; CDS 3: 3673–3813; CDS 4: 4595–4705; CDS 5: 5608–5749; CDS 6: 6445–6542; polyA site: 6636.

FIG. 5 is a mouse cDNA sequence (SEQ ID NO:15) for preAMP-18.

FIG. 6 is mouse preAMP-18 amino acid sequence (SEQ ID NO: 16); RT-PCR performed on RNA isolated from mouse stomach antrum: Y-21 is the predicted N-terminus of the mature protein; the spaces indicated by . . . mean there are no nucleotides there to align with other sequences in FIG. 11.

FIG. 7 is a cDNA (SEQ ID NO: 17) expressing porcine AMP-18.

FIG. 8 is pig pre-gastrokine (pre-AMP-18) protein sequence (SEQ ID NO: 18) predicted from cDNA clone based on Powell (1987) D-21 is the N-terminus of the mature protein—confirmed by sequencing of the protein isolated from pig stomach.

FIG. 9 is a comparison between the amino acid sequences of human (SEQ ID NO: 13) versus pig (SEQ ID NO: 18) pre-gastrokine.

FIG. 10 shows a computer-generated alignment comparison of human (SEQ ID NO:13), pig (SEQ ID NO: 18) and mouse (SEQ ID NO: 16) predicted protein sequences determined from sequencing of cDNA clones for human and pig AMP-18, and by polymerase chain reaction of mouse RNA and DNA using preAMP-18 specific oligonucleotide primers; in each case the first 20 amino acids constitute the signal peptide, cleaved after passage through the endoplasmic reticulum membrane.

DETAILED DESCRIPTION OF THE INVENTION

1. General

Figure 11:
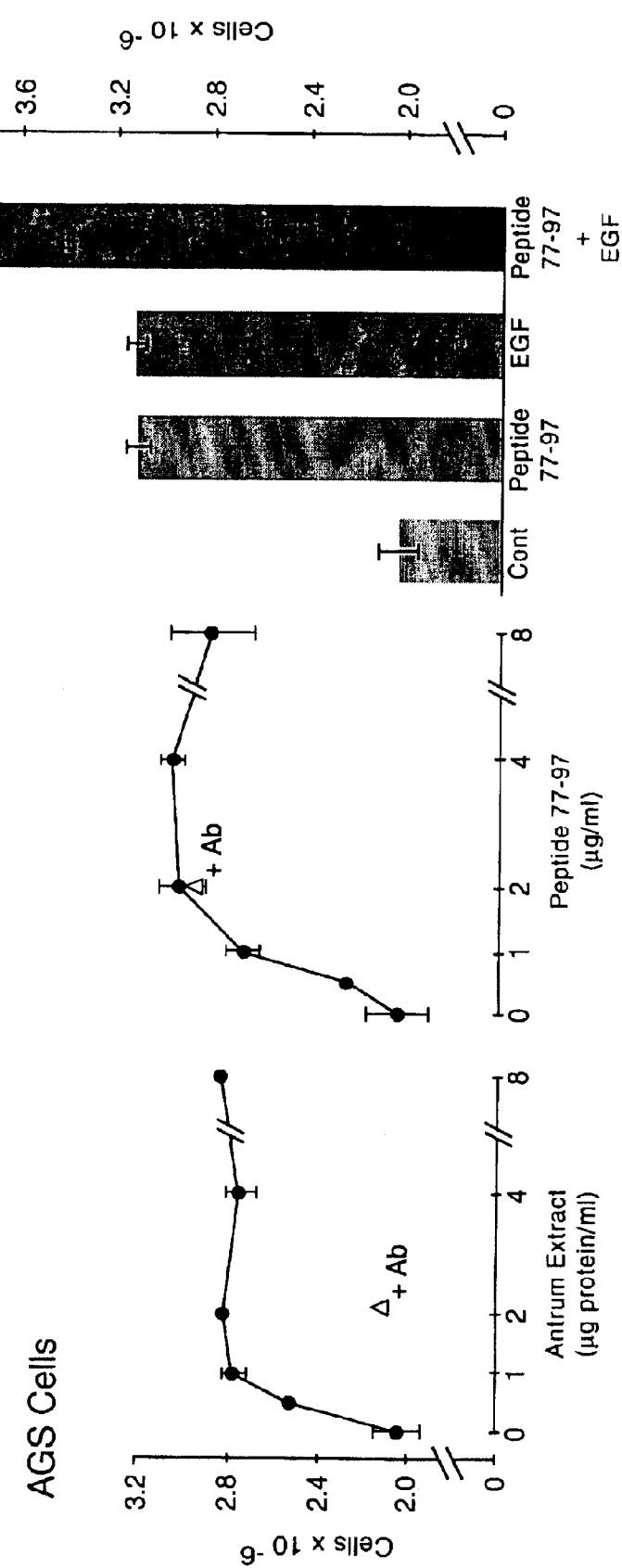
FIG. 11 shows the effect of porcine gastric antrum mucosal extract, human AMP peptide 77–97, and EGF on growth of gastric epithelial cells; AGS cells were grown in DMEM containing fetal bovine serum (5%) in 60-mm dishes; different amounts of pig antrum extract, HPLC purified peptide 77–97, and/or EGF were added; four days later the cells were dispersed and counted with a hemocytometer; antrum extract and peptides each stimulated cell growth in a concentration-dependent manner; the bar graph shows that at saturating doses, peptide 77–97 (8 g/ml) or EGF (50 ng/ml) was mitogenic; together they were additive suggesting that the two mitogens act using different receptors and/or signaling pathways; anti-AMP antibodies inhibited the antrum extract but did not inhibit peptide 77–97.

A novel gene product, a member of a group of gastrokines, was detected in mammalian gastric antrum mucosal by a differential screen of cDNA libraries obtained from different regions of the pig stomach. The cDNA sequence predicted a protein of 185 amino acids including a signal peptide leader sequence. A cDNA was also isolated from a human library. The predicted amino acid sequence identity between pig and human in 76.3%. The sequences predicted a 20 amino acid signal peptide characteristic for secreted proteins. The cleavage of this N-terminal signal peptide was confirmed for the pig protein. Antibodies to the product of the human cDNA expressed in bacteria were raised in rabbits; these antibodies reacted with 18–20 kD antrum antigens of all mammalian species tested (pig, goat, sheep, rat and mouse). In agreement with mRNA levels, the AMP-18 protein is expressed at high levels only in the gastric antrum; it is barely detectable in the rest of the stomach or duodenum, and was not detected in a variety of other tissues tested. AMP-18 is synthesized in the lumenal surface mucosal cells; immuno-electron microscopy locates AMP-18 in the secretion granules of these cells. Partially purified AMP-18 preparations from mouse and pig antrum tissue are mitogenic to confluent stomach and kidney epithelial cells in culture; this effect is inhibited by the specific antisera, implying that AMP-18, or its products, is a growth factor.

AMP-18 is likely secreted with the mucus and functions, perhaps as peptide derivatives, within the mucus gel to maintain epithelial integrity directly, and possibly to act against pathogens. In view of the growth factor activity observed on epithelial cell lines in culture, it is likely that AMP-18 or its peptide derivative(s) serves as an autocrine (and possible paracrine) factor for the gastric epithelium. The function of AMP-18 may not be simply as a mitogen, but in addition it may act as differentiation factor providing the signals for replenishment of the mature lumenal surface cells. The AMP-18 protein or its derivatives are likely important to the normal maintenance of the highly dynamic gastric mucosa, as well as playing a critical role in the restitution of the antrum epithelium following damage. This protein has not been characterized in any publication, however, related nucleic acid sequences have been reported as ESTs and as a similar full length gene. Limitations of EST data cannot yield information on starting sequences, signal peptides, or sequences in the protein responsible for bioactivity, as disclosed in the present invention. A number of these ESTs have been reported for mammalian stomach cDNAs, but related ESTs have also been reported or pancreas and also pregnant uterus libraries. Although expression of AMP-18 RNA in these other tissues appears to be low (as indicated for pancreas by PCR analysis), these results suggest that this growth factor may have broader developmental and physiological roles than that implied by the specific high levels of expression found for the stomach.

The AMP-18 protein appears to be expressed at the surface of the cellular layers of the gastrointestinal (GI) tract. The expressing cells may be releasing stored growth factor where needed—in the crypts and crevices of the GI tract where cellular repair is needed due to surface damage.

AMP-18 may act on the mucosal, apical surfaces of the epithelial cells, collaborating with prostaglandins and other growth factors that operate via basolateral cell surface receptors on the serosal side. The protein or its derivatives are likely important for the normal maintenance of the highly dynamic gastric mucosa, in face of the mechanical stress and high acidity of the stomach. AMP-18 may play a critical role in the repair of the stomach epithelium following damage by agents such as alcohol, nonsteroidal anti-inflammatory drugs (NSAIDs), or pathogens, in particular *Heliobacter pylori*, which predominantly infects the antrum and is a causative agent of gastric ulcers and possibly cancers.

2. Bioactivity

A synthetic peptide (42 amino acids, a "42-mer") representing a central region of the AMP-18 amino acid sequence also has growth factor activity, which is inhibited by specific antisera; some related shorter peptides also have stimulatory activity, while others can inhibit the activity of the 42-mer. This result suggests that a saturable epithelial receptor exists for AMP-18, and opens direct avenues to analyzing the bioactive regions of the protein and identifying the putative receptor(s). Because AMP-18 does not resemble in structure any known cytokine or cytoprotectant protein (such as the trefoil peptides), the analysis of the interactions of the protein, and its active and inhibitory related peptides, with cells offers the opportunity to reveal novel molecular interactions involved in cell growth control.

BSC-1 cell growth was stimulated by gel-fractionated porcine antrum extract; porcine extract protein (250 $\mu$g) was loaded into each of 2 lanes and subjected to electrophoresis in a polyacrylamide gel (12.5%); the 5 thin slices (2–3 mm) from each area between $M_r$ 14 kDa and 21.5 kDa were cut from the experimental lanes. Each pair of slices was placed in a silanized microfuge tube with 200 $\mu$l sterile PBS, 3% acetonitrule and 1% BSA, and macerated; proteins were eluted from the gel for 18 hr at 22° C. with vigorous shaking; the samples were then microcentrifuged and a sample of a supernatant was added to a confluent culture of BSC-1 cells; the number of cells was counted 4 days later; maximal growth stimulation was observed in cultures receiving extracts eluted from gel slices corresponding to a $M_r$ of ~18 kDa; antisera to recombinant human AMP-18 added to the culture medium completely inhibited growth stimulation by the 18 kDa fraction (+Ab); values are means of 2 cultures; SE is less than 10% of the mean.

The biological activity (mitogenic for epithelial cells in the gastro-intestinal tract) of the AMP-18 is located in the C-terminal half of the protein. The epitopic sequence(s) appear(s) to be immediately N-terminal to the mitogenic sequence.

The biological activity that is a growth factor, is exhibited by a peptide comprising at least 42 amino acids from positions 78 to 119 of the full-length protein sequence. An antibody to this region blocked mitogenic activity. Although a peptide having an amino acid sequence of 104 to 117 had mitogenic activity, an antibody to this region did not block (inhibit) the activity. A peptide with an amino acid sequence from positions 97–117 has the same mitogenic activity as a peptide with the 42 amino acid sequence, but is less expensive to produce as a synthetic peptide.

3. Inhibition of Bioactivity

Epithelial cell growth that was stimulated by murine or porcine antrum cell extract was blocked by rabbit antiserum to a complete, recombinant human AMP-18 precursor protein; confluent cultures of BSC-1 cells were prepared; murine or porcine antrum cell extract was prepared and its protein concentration was measured; cell extracts alone and with different dilutions of the antiserum, or antiserum alone (1:100 dilution was added to the culture medium, and the number of cells was counted 4 days later). Growth stimulation by murine antrum gastrokines was maximally inhibited by the antiserum (93%) at a dilution of 1:400, whereas stimulation by the porcine antrum protein extract was totally inhibited at a dilution of 1:100. Scored values were means for 3 cultures; standard error of the mean (SE) was less than 10% of the mean.

Antibodies to the AMP-18 protein have diagnostic uses to determine different levels of the protein in the gastro-intestinal tract in vivo. Ulcers are likely to develop if less than normal levels of AMP-18 protein are present. Normal values are determined by technologies known to those of skill in the art, that is, obtaining representative samples of persons to be tested (age, sex, clinical condition categories) and applying standard techniques of protein quantitation. The effects of aspirin and indamethacin on AMP-18 levels are also useful to monitor deleterious levels of the drugs including the non-steroidal anti-inflammatory drugs (NSAIDs). Stomach cancer cell lines do not express the AMP-18 proteins at least by detection methods disclosed herein.

4. Genomic DNA

Genomic AMP-18 DNA sequences have been cloned for human and mouse as a prelude to the analysis of the gene regulatory elements, which presumably determine the great differences in the levels of expression of the gene in tissues where the gene may be active. Upstream and downstream flanking sequences have been isolated from mouse genomic DNA preparatory to a gene knockout. The flanking genomic sequences likely determine the very different levels of expression of the gene in the stomach and few other tissues where it may be expressed. With the involvement of different regulatory elements, gastrokine genes could be expressed as a growth factor in other tissues.

5. Uses of Gastrokines of the Present Invention

Because the AMP-18 protein and certain peptides derived from it can stimulate growth and wound repair by stomach and intestinal epithelial cells (as well as kidney) these gastrokine molecules are candidates for therapeutic agents to speed recovery of the injured GI tract following pharmacological interventions, radiotherapy, or surgery. In addition, the antibodies developed to gastrokines may be used in kits to measure the levels of AMP-18 protein or peptide in tissue of blood in diverse pathological states. These novel molecules have great therapeutic potential in the treatment of gastric ulcers, and inflammatory bowel disease, whereas new agents that inhibit its function could prove useful in the treatment of cancers of the GI tract.

The stomach is not a congenial location for many bacteria, and those that can survive the acidity do not establish themselves there (Rotimi et al., 1990). It is of interest therefore that the antrum region is the favored site for the attachment, penetration and cytolytic effects of *Helicobacter pylori*, an agent which infects a major proportion of the human population (>60% by the seventh decade) and has been associated with gastritis, gastric and duodenal ulcers (Goodwin et al., 1986; Blaser, 1987) and gastric adenocarcinomas (Nomura et al., 1991; Parsonnet et al., 1991). Thus as an epithelial cell growth factor, AMP-18 may act to ameliorate the damage caused by bacterial infiltration and cytolysis. Given the conjunction of the specific antrum expression of AMP-18 and the preferred site of binding of *H. pylori*, it is possible that the bacteria use AMP-18 as a tropic factor. *H. pylori* attaches to cells of the antrum having fucose-containing mucin granules (Falk et al., 1993; Baczako et al., 1995). These granules also may contain AMP-18. Anti-microbial peptides have been found in the stomach of the amphibian *Xenopus laevis* (Moore et al., 1991). Some domains of the AMP-18 structure resemble that of the magainins, and possibly AMP-18 interacts with enteric bacteria.

6. Isolation of Pig AMP-18

Antisera against human AMP-18 protein were used to assist in the purification of the protein from extracts of pig antrum mucosa. Immnoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus the one predicted by cleavage of 20 amino acids from the N-terminus of the ORF precisely at the alanine-aspartate site anticipated for signal peptide removal. Despite the abundance of asparagine residues in the mature protein, none fit the consensus context characteristic of glycosylation. Fairly extensive regions of the protein may possess amphipathic helix forming propensity. The latter may represent units within the protein yielding bioactive peptides after processing. Using circular dichroism the synthetic peptide representing amino acids 126–143 in the human preAMP sequence (FIG. 3) is readily induced to become helical in moderate concentrations of trifluoroethanol conditions used to assess helix propensity for some bioactive peptides, including anti-microbial peptides of the magainin type (see, for example, Park et al., 1997).

Materials and Methods

1. Isolation of Antrum-Specific cDNA Clones cDNA clones for the gastrointestinal (GI) peptide gastrin, which regulates gastric acid secretion as well as mucosal and pancreatic cell growth (Yoo et al., 1982) were isolated. From these screens several other mRNAs expressed relatively specifically in the antrum of the stomach were found. The open reading frame (ORF) in one of these RNAs was highly conserved between pig and man, and predicted a novel conserved protein of no immediately apparent function. Using specific antibodies, it was shown that similar protein species are present in the stomach antrum mucosa of all mammals tested. There is tissue specificity of expression of these sequences and they are apparently ubiquitously present in the antrum mucosa of mammalian species.

2. RNA Expression

The isolation of the cDNA clones was predicted on a preferential expression in the mucosa of the stomach antrum and this has been confirmed initially by Northern blot hybridization of RNAs from various tissues probed with the cDNA sequences and subsequently by protein analysis. The Northern blots showed the specificity of mRNA expression within the gastrointestinal tract of the pig. Highest mRNA expression was in the antrum mucosa, variable amounts in the adjacent corpus mucosa and undetectable levels in fundus, esophagus and duodenum. The non-mucosal tissue of the antrum and corpus contained little RNA reacting with the cDNA probe.

3. Antibodies to Expressed Protein

The open reading frames (ORFs) of the human and pig cDNA clones predict very similar relatively low molecular weight (MW) proteins, which have no close homologs to known proteins in the computer databases and therefore give little indication of possible function. As an approach to study the biological role of the presumptive proteins, the full cDNA sequences were expressed in *E. coli*, using a vector that also encoded an N-terminal His6-tag. Unfortunately, as expressed in bacteria the polypeptide products are insoluble and not readily amenable to biochemical studies. However, the bacterial product of the human cDNA was separated on sodium dodecyl sulfate (SDS) gels used as an immunogen in rabbits to elicit antisera. The sera were screened against protein extracts of antral tissue from a number of mammalian species. This procedure has successfully produced several high-titer, low background antisera capable of recognizing both the immunogen and proteins of about 18 kDa expressed in the antrum of the mammals tested. The bacterially-expressed protein migrates more slowly because it contains the signal peptide sequence was well as a His6-tag. The preimmune sera showed no significant 18 kDa reactivity. The cross-reactivity of the antisera raised against the protein expressed from the human cDNA clone with proteins of very similar MW in antrum extracts from a variety of mammals (pig, goat, sheep, rat and mouse; the last consistently migrates slightly more rapidly in SDS gels) supports the level of conservation of amino acid sequence predicted by comparison of the ORFs of the human and pig cDNAs (See FIG. 11). In subsequent experiments, human AMP-18 with a signal peptide was produced in bacteria.

The preimmune sera give insignificant reactions on Western blots of all tissue extracts, while the two immune sera (at up to 1:50000 dilution) both give major bands of 18–20 kDa only, and those only in stomach antrum extracts, and to a lesser degree in the adjacent corpus extracts. The sera were raised against bacterially-expressed protein so there is no possibility of other exogenous immunogens of animal origin.

As determined by immunoblots, the specificity of expression to the antrum is even greater than the Northern blots would suggest, and the strength of the signal from antrum extracts implies a relatively high abundance of the protein, although quantitative estimates were not made. Significant antigen was not detected in non-stomach tissues tested.

The immunohistochemistry showed insignificant staining of antral tissue by both preimmune sera, while both immune sera stained the surface mucosal cells very strongly at considerable dilutions. The preimmune sera did not lead to immunogold staining in the immunoelectron microscope study. The growth factor activity of antrum extracts is inhibited by both immune, but not preimmune sera. Finally, the results with a synthetic peptide, which has growth factor activity, is inhibited by the immune but not the preimmune sera, and carries epitopes recognized by the immune but not the preimmune sera, further validate the specificity of these reagents.

4. Northern Blot Hybridization of RNAs from Pig Gut Mucosal Tissues

Total RNA was electrophoresed, transferred to a membrane and hybridized with a labeled pig AMP-18 cDNA probe. The source of the RNA sample for each lane was: 1. Distal duodenum; 2. Proximal duodenum; 3. Antrum; 4. Adjacent corpus; 5. Fundus; 6. Esophagus. Equal amounts of RNA were loaded. The signal from RNA of the antrum adjacent corpus was variable. Size markers (nucleotides) were run on the same gel for comparison.

5. Immunoblots Using a Rabbit Antiserum Raised Against the Bacterial-Expressed Protein Directed by the Human Antrum-Specific cDNA Clone Whole tissue proteins were dissolved in SDS buffer, electrophoresed, and transferred to membranes that were reacted with immune serum (1:50000). Bound antibody molecules were detected using peroxidase-labeled anti-rabbit antibody. Preimmune serum gave no specific staining of parallel blots at 1:200 dilution. Lanes: 1, 6, 13, 17 contained markers. 2 HeLa cells. 3 mouse TLT cells. 4 expressed human protein+HELA cells. 7 mouse corpus. 8 mouse antrum. 9 mouse duodenum. 10 mouse intestine. 11 mouse liver. 12 expressed human protein+TLT cells. 14 mouse antrum. 15 mouse brain. 16 mouse Kidney. 18 pig antrum. 19 mouse antrum.

Immunoblots of high percentage acrylamide gels showed that the antisera recognized epitopes on the synthetic peptide 78–119. The reaction of peptide 78–119 with the antibodies was not unexpected because this region of the sequence was predicted to be exposed on the surface of the protein and to be antigenic. Not only does this further substantiate a belief that AMP-18 or its immediate precursor, is a growth factor, for epithelial cells, but also provides a basis for analysis of the bioactive (and antigenic) regions of AMP-18, and a tool for the assessment of cell receptor number and identity. Chemical synthesis of peptides also makes available a convenient and rapid source of considerable quantities of pure "wild-type" and "mutant" reagents for further cell studies. The synthetic peptide 78–119 apparently acts by the same mechanism as the antrum protein, because their maximal effects are not additive.

6. Sequence and Predicted Structure of the Pre-AMP Open Reading Frame

The predicted amino acid sequences for human and pig are 76% identical. The predicted signal peptides are not bold; the N-terminus of native pig AMP has been shown to be aspartate (FIG. 11).

7. Structure of the Native Protein

The ORF's of the human and pig cDNAs predicted polypeptides of similar general structure (FIG. 11). The predicted molecular weights for the otherwise unmodified human and pig proteins was 18.3 and 18.0 respectively; these values are in good agreement with electrophoretic mobility in SDS the of antrum proteins reacting with the antisera of the present invention.

The antisera was used to assist in the purification of the protein from extracts of pig antrum mucosa. Immnoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus is one predicted by cleavage of about 20 amino acids from the N-terminus of the ORF precisely at the alanine-aspartate site anticipated for signal peptide removal. Despite the abundance of asparagine residues, none fit the consensus context for glycosylation. Fairly extensive regions which may possess amphipathic helix forming propensity. The latter may represent units within the protein or as peptides after processing. Using circular dichroism the synthetic peptide representing amino acids 126–143 in the human preAMP sequence (FIG. 3) is readily induced to become helical in moderate concentrations of trifuoroethanol conditions used to assess helix propensity for some bioactive peptides, including anti-microbial peptides of the magainin type (see for example Park et al., 1997).

8. Localization of AMP-18

The antisera to AMP-18 have proven to be excellent histochemical probes, reacting strongly with sections of the mouse antrum region but not with the fundus, duodenum or intestine, confirming the results of the immunoblots. The preimmune sera give negligible reactions even at much higher concentration. The AMP-18 protein appears to be concentrated in mucosal epithelial cells lining the stomach lumen, although lesser signals in cells deeper in the tissue and along the upper crypt regions suggest that cells may begin to express the protein as they migrate toward the lumenal layer. Higher magnification of the histochemical preparations indicates only a general cytoplasmic staining at this level of resolution; there are some patches of intense staining that may be the light microscope equivalent of granule-packed regions of some lumenal surface cells seen by electron microscopy (EM). The localization of AMP-18 in the antrum mucosa is therefore very different from those cells synthesizing gastrin which are deep in the mucosal layer.

9. Immunoelectron Microscope Localization of the AMP-18 Antigens in the Mouse Stomach Antrum Mucosal Cells The tissue pieces were fixed in 4% formaldehyde and processed for embedding in Unicryl. Thin sections were reacted with rabbit anti-human AMP-18 antisera (1:200); bound antibodies detected by Protein-A conjugated to 10 nm colloidal gold. The reacted sections were stained with lead citrate before viewing (20,000×). The gold particles are visible over the semi-translucent secretion granules, which appear much more translucent here than in the standard glutaraldehyde-osmium-epon procedure (11,400×) because of the requirements for immuno-reactivity. Negligible background was seen on other cytoplasmic structures.

The general structure of the protein implies a possible secretory role so a precise intracellular localization would be valuable. This requires EM immuno-cytochemical procedures. Standard embedding and staining methods reveal that, as previously reported by many others, the antrum region (e.g. Johnson and McMinn, 1970) contains mucosal epithelial cells which are very rich in secretory granules. Preliminary immuno-EM data show the immune sera used at 1:200–1:800 dilution react specifically with the secretion granules. The latter appear somewhat swollen and less electron opaque than in standard fixation conditions and the differences in density are harder to discern, but overall the cell structure is quite well-preserved for stomach tissue fixed and embedded under the less stringent conditions required to preserve immuno-reactivity. At 1:100 dilution, the preimmune sera exhibited negligible backgrounds with no preference for the secretion granules.

10. Growth Factor Activity on Epithelial Cell Cultures.

A possible function for AMP-18 is that it is a growth factor at least partly responsible for the maintenance of a functional mucosal epithelium in the pyloric antrum and possibly elsewhere in the stomach. Initially, stomach epithelial cell lines were not immediately available, but kidney epithelial cell systems (Kartha et al., 1992; Aithal et al., 1994; Lieske et al., 1994) were used. A fractionated antrum mucosal cell extract was used for these experiments. Using immunoblotting as a probe to follow fractionation, on lysis of the mucosal cells scraped from either pig or mouse antrum, the AMP-18 antigen was recovered in the 35S fraction on sucrose density gradients. Such high speed supernatant fractions served as the starting material for studies on cell growth. Unexpectedly, these extracts stimulated a 50% increase in confluent renal epithelial cells of monkey (BSC-1 cells), but had no effect on HeLa or WI-38 fibroblast cells. The stimulation of BSC-1 cells was at least as effective as that observed with diverse polypeptide mitogens, including EGF, IGF-I, aFGF, bFGF and vasopressin, assayed at their optimal concentrations. Comparable growth stimulation by the antrum extracts was observed when DNA synthesis was assessed by measuring [$^3$H]thymidine incorporation into acid-insoluble material. The biological activity of the antrum extracts survived heating for 5 minutes at 65° C., and dialysis using a membrane with $M_r$ cutoff of 10 kDa, which would eliminate most oligopeptides; this treatment removes 60–70% of polypeptide material, but spared AMP-18 as assayed by immunoblots. More importantly, mitogenic stimulation of BSC-1 cells by the mouse or pig antrum extract was inhibited when either of two different antisera to the human recombinant preAMP-18 (expressed in bacteria) was added to the culture medium. Preimmune sera (1:100 to 1:800) had no effect on cell growth, nor did they alter the mitogenic effect of the antrum extracts. These observations suggest that gastric mucosal cell AMP-18 functions as a potent mitogen for kidney epithelial cells, which do not normally express this protein.

To gain further evidence that the growth-promoting activity in the partially fractionated antrum extracts was mediated by the AMP-18 protein, an aliquot of the mouse extract was subjected to SDS-polyacrylamide gel electrophoresis; the method used previously to determine the N-terminal sequence of the natural protein. The gel was cut into 2-mm slices and each slice was extracted with 3% acetonitrile in phosphate-buffered saline containing 1% BSA. The extract supernatants were assayed for mitogenic activity. The results indicated that one slice containing protein in the 16–19 kDa range possessed growth-promoting activity. Significantly, this growth response was blocked by the immune but not the pre-immune sera. Taken together with the relatively low sedimentation rate of the protein, these findings provide additional evidence to support the conclusion that AMP-18 is an epithelial cell mitogen and that it functions as a monomer or possibly a homotypic dimer. It also implies that eration by acting on different cell surface receptors. It also implies that AMP-18 growth factor activity might normally collaborate with other autocrine and paracrine factors in the maintenance or restitution of the epithelium. In view of the results with EGF, it is likely that AMP-18 is secreted at and acts upon the apical face (i.e., stomach lumenal face) of the epithelial cell layer while other factors (for which EGF may serve as an example) act from the basal surface.

11. Bioactivity of Gastrokine (AMP-18) Related Peptides.

The activities of synthetic peptides of the present invention are unexpected. Peptides based on the ORF of the human cDNA clone peptides were synthesized in the University of Chicago Cancer Center Peptide Core Facility, which checks the sequence and mass spectra of the products. The peptides were further purified by HPLC. Five relatively large oligopeptides (of about 40 amino acids each) approximately spanning the length of the protein without including the signal peptide, were analyzed. One peptide 42 amino acids long spanning amino acids lys-78 to leu-119 of the pre-AMP sequence (peptide 58–99 of the matured form of the protein; see Table 1), including a predicted helix and glycine-proline (GP) turns, gave good mitogenic activity. This response was blocked by the specific antiserum, but not by the preimmune sera.

| Name of Peptide, Sequence in Human | #AA | AMINO ACID SEQUENCE | $K_{1/2}, \mu M$ |
|---|---|---|---|
| 78–119 | 42 | KKTCIVHKMKKEVMPSIQSLDALVKEKKLQGKGPGGPPPKGL (SEQ ID NO:6) | 0.3 |
| 78–88 | 11 | KKTCIVHKMKK(SEQ ID NO:4) | Inactive |
| 87–105 | 19 | KKEVMPSIQSLDALVKEKK(SEQ ID NO:5) | Inactive |
| 104–117 | 14 | KKLQGKGPGGPPPK(SEQ ID NO:3) | 0.8 |
| 104–111 | 18 | KKLQGKGPGPPPKGLMY (SEQ ID NO:7) | 1.0 |
| 97–117 | 21 | LDALVKEKKLQGKGPQGPPPK(SEQ ID NO:8) | 0.3 |
| 97–117** | 21 | GKPLGQPGKVPKLDGKEPLAK(SEQ ID NO:9) | Inactive |
| 97–121 | 25 | LDALVKEKKLQGKGPGGPPPKGLMY(SEQ ID NO:10) | 0.2 |
| 109–117 | 9 | KGPGGPPPK(portion of SEQ ID NO:10) | 2.5 |
| 104–109 | 6 | KKLQGK(portion of SEQ ID NO:10) | 7.4 |
| 110–113 mouse | 4 | GPGG(portion of SEQ ID NO:10) | Inactive |
| 97–119 | 23 | LDTMVKEQKGKGPGGAPPKDLMY(SEQ ID NO:2) | 0.2 | the structure of the protein such that it can readily reacquire a native conformation after the denaturing conditions of SDS-gel electrophoresis.

Figure 12:
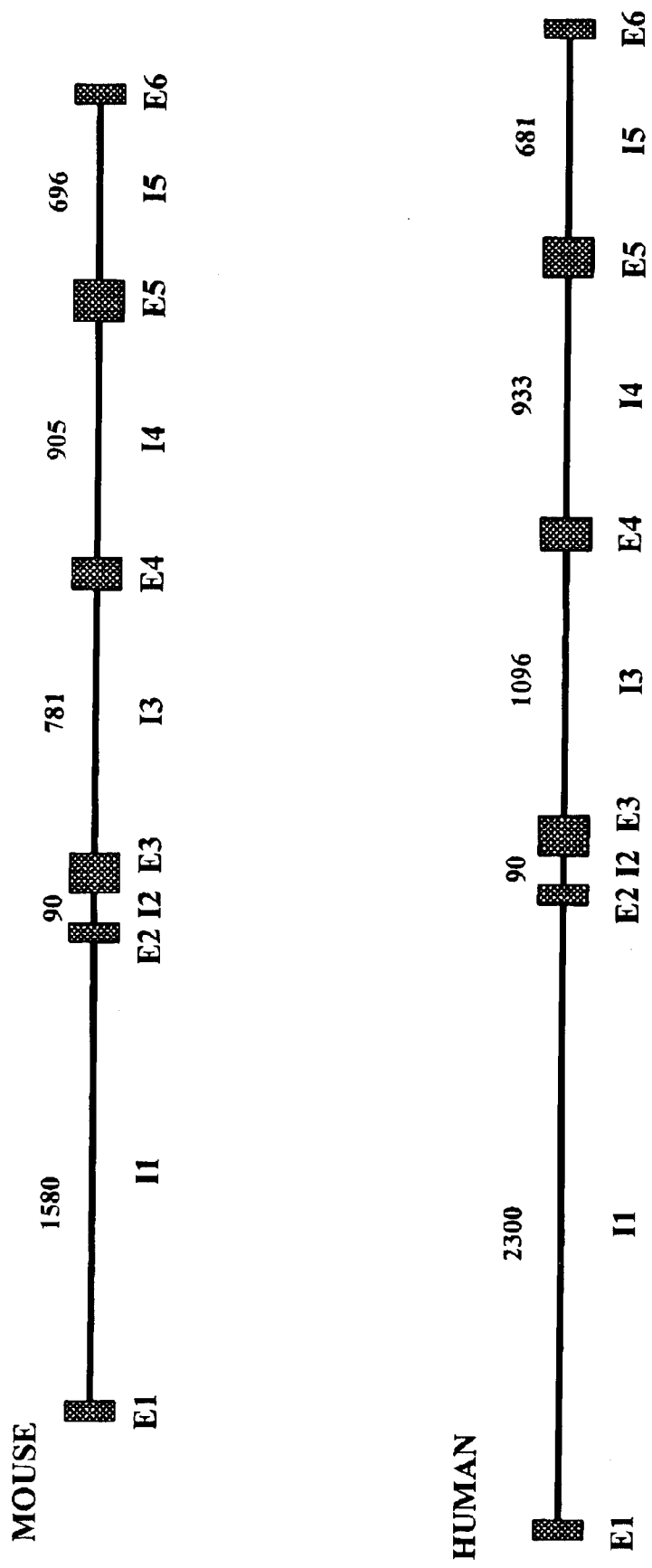
FIG. 12 shows the structure of the human and mouse preAMP-18 genes; the number of base pairs in introns are shown above the bars; exons are indicated E1–E6 and introns 11–15; there are minor differences in intron length.

To assess the interaction of the antrum growth factor activity with other cytokines, its activity was tested to determine if it was additive with EGF in epithelial cell cultures. EGF (50 ng/ml) added with untreated mouse antrum extract (10 μg/ml), or heated, dialyzed pig extract (10 μg/ml) exhibited additive stimulation of mitogenesis; up to 74% increase in cell number above the quiescent level; the greatest stimulation observed so far for any factor using the BSC-1 cell assay. An example of this additivity is shown for an AMP-peptide and EGF on AGS cells in FIG. 12. This observation suggests that AMP-18 and EGF initiate prolif- Table 1: Analysis of Mitogenic Peptides Derived from the Human and Mouse Gastrokine (AMP-18) Sequence. A 14 amino acid mitogenic domain is in bold type. *Peptides are identified by their position in the amino acid sequence of the pre-gastrokine (preAMP-18). #AA: number of amino acids in a peptide. $K_{1/2}$: concentration for half-maximal growth stimulation.

Overlapping inactive peptides can inhibit the activity of the mitogenic peptides: that is, human peptides 78–88 and 87–105 block the activity of peptide 78–119, and while peptide 87–105 blocks the activity of peptide 104–117, the peptide 78–88 does not. Peptides 78–88 and 87–105 block the activity of the protein in stomach extracts.
**scrambled 12. The Growth Stimulatory Domain of Gastrokine (AMP-18).

Finding that a 42-amino acid peptide representing a central region of the novel antrum mucosal cell protein AMP-18 had mitogenic activity similar in character to that of the intact protein in pig and mouse antrum extracts (Table 1), has facilitated the characterization of the bio-active region of the molecule. A peptide including amino acids at positions 78–119, gave similar maximal stimulation of growth of the BSC-1 epithelial cell line to that given by the tissue extracts and was similarly inhibited by several different antisera raised in rabbits to the bacterially-expressed complete antrum protein. The mitogenic activity of a number of synthetic "deletion" peptides related to peptide "78–119" are summarized in Table 1. Growth activity determinations have so far been accomplished with the kidney epithelial cell line as well as several gastric and intestinal lines.

The original 42 amino acid sequence of peptide 78–119 was broken into three segments bounded by lysine (K) residues; N-terminal to C-terminal these are peptides with amino acids at positions 78–88, 87–105 and 104–117. Of these only peptide 104–117 possessed mitogenic activity giving a similar plateau of growth stimulation but requiring a higher molar concentration than the original peptide "78–119"; this is reflected in the higher $K_{1/2}$ value, which suggests that 14-amino acid peptide has 30–40% of the activity of the 42-amino acid peptide. A conclusion from this is that the smaller peptide has less binding affinity for a cell receptor, perhaps due to a lessened ability to form the correct conformation, or alternatively because of the loss of ancillary binding regions. The latter notion is supported by the observations that peptides "78–88" and "87–105" can antagonize the activity of intact 42-mer peptide 78–119; these peptides also antagonize the activity of antrum extracts further supporting the validity of synthetic peptides as a means to analyze the biological function of the novel protein. An additional aspect of the invention is that peptide 87–105, but NOT 68–88, antagonizes the activity of peptide 104–117; note that peptide 87–105 overlaps the adjacent 104–117 sequence by two residues.

Taken together these results suggest a relatively simple linear model for the growth-stimulatory region of AMP-18; viz, there is an N-terminal extended binding domain (predicted to be largely helix, the relative rigidity of which may explain the linear organization of the relevant sequences as determined in the cell growth studies), followed by a region high in glycine and proline with no predicted structure beyond the likelihood of turns. It is this latter region which contains the trigger for growth stimulation. The specificity of antagonism by peptides 78–88 and 87–105 may be based on whether they overlap or not the agonist peptides 78–119 and 104–117; for example 78–88 overlaps and inhibits 78–119, but does not overlap or inhibit 104–117. The specificity of competition by these peptides taken with the inactivity of the 78–119 scrambled peptide, strengthens a conclusion that AMP-18 interacts with specific cellular components. Further evidence that the receptor binding region extends N-terminally from peptide 104–117 is provided by the enhanced activity of peptide 97–117 which contains a seven amino acid N-terminal extension of 104–117. A peptide with a four amino acid extension in the C-terminal direction (peptide 104–121) appears to have slightly less activity to the parent 104–117, but does include a natural tyrosine, which makes possible labeling with radioactive iodine, which allows determination of the binding of AMP-related peptides to cells, initially by assessment of number of binding sites and subsequently detection of the receptor protein(s).

The peptide 97–107 was used for most tests because of its activity (equal to the 42-mer) and its relative economy (21 amino acids in length). However, a C-terminal extension to the tyr-121 gives the most active peptide thus far, perhaps because it stabilizes secondary structure. Even though this peptide does not match the nanomolar activity of EGF, for example, it is much more potent than reported for trefoil peptides (Podolsky, 1997). An estimate for the activity the intact AMP protein is ca. 1–10 nM.

13. Expression of Recombinant Protein (a) *E. coli*. Recombinant constructs are generally engineered by polymerase-chain-reactions using synthetic oligonucleotides complementary to the appropriate regions of the full-length cDNA sequences within the PT/CEBP vector and extended by convenient restriction enzyme sites to enable ready insertion into standard vector polylinkers. The initial experiments with expression of the AMP ORF in bacterial systems employed an expression vector PT/CEBP, which included an N-terminal His6-tag (Jeon et al., 1994), intended to facilitate the purification of the expressed protein on Ni-NTA resin (Qiagen). Expression of the full-length human cDNA within this vector in the host BL21(DE3)pLyS gave good yields of insoluble protein, which after electrophoresis under denaturing conditions was suitable for use as an immunogen in rabbits to obtain specific high-titer antibodies, but which has not been useful for analysis of the protein's native structure and function. This insolubility most probably due to the presence of an unnatural N-terminus, having a His6-tag upstream of hydrophobic signal peptide, in the expressed protein. Engineering vectors which will express the ORF without the hydrophobic signal peptide sequence are also useful. These are constructed using bacterial expression vectors with and without N- or C-terminal His-tags. The human AMP-18 sequence lacking the 20 amino acid signal peptide and containing a His6-tag was also expressed in bacteria.

(b) *Pichia pastoris*. Among the simple eukaryotes, the budding yeast *P. pastoris* is gaining wide popularity as an expression system of choice for production and secretion of functional recombinant proteins (Romanos et al., 1992; Cregg et al., 1993). In this system, secretion of the foreign protein may utilize either its own signal peptide or the highly compatible yeast mating-type alpha signal. This organism will correctly process and secrete and at least partially modify the AMP-18 protein. Vectors for constitutive and regulated expression of foreign genes are developed in Pichia (Sears et al., 1998). In addition to a poly-linker cloning site, these vectors contain either the high expression constitutive glyceraldehyde-3-phosphate dehydrogenase (GAP) or the methanol-regulated alcohol oxidase promoter (AOX1). The latter is an extremely stringent promoter yielding insignificant product in normal culture conditions while giving the highest expression of the vectors tested in the presence of methanol, amounting to as much as 30% of the cell protein. The advantage that the yeast Pichia has over the mammalian and insect alternatives is that it is continuously grown in protein-free media, thus simplifying the purification of the expressed protein and eliminating extraneous bioactivities originating in the serum or the host animal cells. A pIB4 construct (inducible by methanol-containing medium) contains the complete human preAMP-18 cDNA sequence.

(c) Baculovirus/Insect cells. An alternative, frequently successful, non-mammalian eukaryotic expression system is that using recombinant Baculovirus, such as *Autographa*

*californica*, in an insect cell culture system. As with Pichia, a large repertoire of convenient vectors are available in this system, containing both glutathione S-transferase (GST)- and His6-tags (Pharmingen). Transfections are carried out into *Spodoptera frugiperda* (Sf) cells; these cells can be slowly adapted to protein-free medium to favor the purification of secreted proteins. If an endogenous signal peptide does not function in these cells, secretion of foreign proteins can also be forced using vectors containing the viral gp67 secretion signal upstream of the cloning site. Recombinant proteins can be expressed at levels ranging from 0.1–50% total cell protein. Some protein modifications may be more favored in this insect cell system relative to yeast, but still may not duplicate the mammalian system. It appears that the insect expression system would be somewhat more onerous than Pichia, and not entirely substitute for expression in mammalian cells. The human AMP-18 sequence lacking the 20 amino acid signal peptide and containing a His6-tag was expressed in Baculovirus.

(d) Mammalian Cells. Modifications not detectable by immunoblot analysis may take place in mammalian cells that are not duplicated in cells of other eukaryotes. Although not as convenient as prokaryotic and simple eukaryotic systems, mammalian cells are now frequently used for both transient and continuous expression of foreign proteins. Several growth factors have been expressed and secreted in significant amounts using these systems.

The plasmid pcDNA3/human kidney 293 system: pcDNA3 contains a polylinker cloning site flanked by the strong constitutive cytomegalovirus (CMV) promoter and a SV40 polyA signal (Invitrogen). Laboratory experience is that 60–90% transient transfection levels can be achieved. To this end, PCR amplification of the human preAMP cDNA clone is performed with oligonucleotides that contain the initiation codon and native ribosome binding site (Kozak sequence) as well as suitable restriction enzyme linkers for correct orientation into pcDNA3. Favorable constructs were identified in the transient assay using the potent antibiotic blasticidin and a vector containing the resistance gene, stable mammalian transfectant cell lines can be established "in less than one week" (Invitrogen). The available vectors also include the constitutive CMV promoter, a polylinker cloning site, an elective V5-epitope/His6-tag and the SV40 poly(A) signal (PcDNA6/V5-His).

14. Expression and Analysis of Altered (Modified) Forms of AMP-18

Given an efficient expression system for the production of "wild-type" AMP-18, a series of mutant proteins, containing either deletions or substitutions may be created, which will permit analysis of the functional domains. The amphipathic helices, the conserved cystine (C) residues and the basic amino acids doublets, which may be cleavage sites, are attractive targets. Although not as simple as an enzyme assay, the mitogenesis assay is routine and replicable, and would enable "mutants" to be characterized as fast as they are constructed. Dominant negative (or positive) "mutants" will be as significant as mutations exhibiting simple loss of function, because these will imply interactions with other factors including possible cell receptors.

15. Biochemical and Immunoaffinity Fractionation of Expressed and Native Gastrokine Proteins In the case of some of the expressed forms of gastrokine AMP-18, the recombinant protein will contain peptide tags that will permit the rapid purification of soluble protein. The presence of these tags, if they do not severely interfere with the protein's normal functions, will also permit analysis of interactions with other relevant macromolecules. His6-tags permit purification by binding the recombinant proteins to Ni-NTA resin beads (Janknecht et al., 1991; Ni-NTA resin from Qiagen). The tagged protein is bound with greater affinity than most antigen-antibody complexes and can be washed rigorously before the $N_1^{2+}$-histidine chelation complex is disrupted by excess imidazole to release the purified protein. GST-tagged recombinant proteins are purified on glutathione-agarose, washed and then eluted with reduced glutathione (Smith and Johnson, 1988). As with all the proposed expression systems, each protein preparation may be tested at the earliest possible stage for its growth factor activity.

Conventional fractionation procedures are used to achieve the desired purity, particularly in the case of the isolation of the natural protein from tissue. Pig antrum mucosa is a preferred starting point for the latter, using initial centrifugation and heat-treatment protocol, followed by a size-exclusion column: BioGel P60 is suitable, given the evidence that the 18 kDa protein exists, most probably as a monomer in the extracts. The eluant is loaded on an immunoaffinity matrix created by crosslinking anti-AMP antibodies purified on HiTrap Protein A to CNBr-activated Sepharose 4B (Pharmacia). Further modification of the immnoaffinity matrix may be helpful, either by extension of the linker to the matrix, which has proven useful in the past (Aithal et al., 1994), or by crosslinking the antibody to immobilized protein-A. Because active protein can be recovered by SDS-gel elution, active protein may also be recovered from the antigen-antibody complexes. Further fractionation could be achieved by C8 reversed-phase high-performance liquid chromatography (HPLC) column. A final step is the use of the SDS-gel elution technique with confirmation of identity by N-terminal sequencing. In all of these steps the immunodetectable AMP-18 and the growth factor activity should fractionate together.

16. AMP-18 Related Synthetic Peptides

AMP-18 may be precursor to one or several bioactive peptides. Synthetic peptides provide a convenient avenue to explore the function of a protein; peptides may mimic aspects of the function or antagonize them. If a peptide either duplicates or inhibits the protein's activity, then it suggests the identity of functional domains of the intact protein, and also provides the possibility of synthesizing specifically tagged probes to explore protein-cell interactions.

Finding that a synthetic 42 amino acid peptide, representing a middle region of the human protein, is capable of mimicking the growth factor activity of the partially fractionated antrum mucosal extracts has provided a short-cut to the analysis of AMP-18 function. This peptide (designated peptide 58–99; amino acids are at positions 58–99 of the mature protein after removal of the signal peptide) in addition to several possible protein processing sites at lysine pairs, contains one of the regions capable of extended helix formation as well as a glycine-proline loop. An added advantage of this peptide is that it contains epitopes recognized by both of the antisera disclosed herein. Some smaller peptides derived from this sequence were synthesized to focus on the bioactive regions. Initially sequences bounded by the lysine residues were studied because they may indicate distinct domains within the protein structure, by virtue of being exposed on the surface of the protein, as witnessed by the antigenicity of this region, and may be sites of cleavage in vivo to bioactive peptides. The glycine-proline region is important (see Table 1 illustrating the bioactive domains of AMP-18). Glycine-proline sequences are known to be involved in SH3 (src homology domain type 3) ligands (see Cohen et al., 1995; Nguyen et al., 1998); because SH domains are involved in protein-protein interactions that GP region of AMP-18 may be involved in the interaction of the protein with a cell surface receptor. The exact GPGGPPP sequence found in AMP-18 has not been reported for the intracellular-acting SH3 domains, so the intriguing possibility exists that it represents a novel protein interaction domain for extracellular ligands. A 21-mer derived from amino acids at positions 97–117 of the mature sequence has activity similar to the 42-mer. This shorter peptide is useful for growth assays on various epithelial cell lines. This peptide does not express the epitope recognized by the antisera disclosed herein.

All of the AMP-18 derived peptides were synthesized by the Cancer Center Peptide Core Facility of the University of Chicago, which also confirmed the molecular mass and amino acid sequence of the purified peptides that are isolated by HPLC. The biological activity of peptide 78–119 not only provides the basis for seeking smaller peptides with mitogenic activity, but permits amino acid substitutions that have positive or negative effects to be found rapidly. Inactive peptides were tested for their ability to block the function of active peptides or intact AMP-18. The possible inclusion of D-amino acids in the peptides (in normal or reverse order) may stabilize them to degradation while permitting retention of biological function. Further the ability to synthesize active peptides enables tags that facilitate studies of the nature, tissue distribution and number of cellular receptors. Such tags include His-6 biotin or iodinated tyrosine residues appended to the peptide sequence (several of the bioactive peptides have a naturally occurring tyrosine at the C-terminus).

Synthetic peptides also permit assessment of the role of potential secondary structure on function. The finding that a 4 amino acid C-terminal extension of the active peptide 97–117, predicted to promote a helix similar to that for the intact AMP-18 sequence, led to a more active peptide 97–121, is interesting. The helix-propensity of these active peptides e.g. peptide 126–143, which resembles an antimicrobial magainin peptide, provides useful information. With respect to anitimicrobial peptides, the function of the magain in class is related to their ability to form amphipathic helices (Boman, 1995). Synthetic peptides that can be locked in the helical form by lactam bridges (Houston et al., 1996) enhanced biological activity; at least one pair of appropriate acidic and basic amino acid residues for lactam formation already exist in potential helix regions of AMP-18.

Another equally significant aspect of the peptide studies is the potential availability of specific anti-AMP-18 peptides that antagonize its biological functions. Tissue culture studies show that sub-peptides of the growth-promoting peptide 78–119 can antagonize the activity of the intact peptide (see Table 1). Peptides that can occupy cellular binding sites but lack some essential residues for activity may block the action of AMP-18 and its active peptides. This makes available another set of reagents for the analysis of cellular receptors and for assessing receptor-ligand affinity constants. Availability of defined peptide antagonists is useful in whole animal studies, and may eventually serve to regulate the activity of the natural protein in humans.

17. Interactions of AMP-18 and Related Peptides with Cells: Assessment of Cell Growth Non-transformed monkey kidney epithelial cell line BSC-1 and other epithelial cell lines were used to assess effects on growth. In general, conditions were chosen for each line such that cells are grown to confluence in plastic dishes in supplemented growth medium with minimal calf (or fetal) serum for growth (Lieske et al., 1997); BSC-1 cells become confluent at $10^6$/60 mm dish with 1% calf serum. At the start of the growth assay the medium on the confluent culture was aspirated and replaced with fresh medium with minimal serum to maintain viability (0.01% for BSC-1) cells. AMP-18 preparations were added to the culture medium and 4 days later the cell monolayer was rinsed, detached with trypsin, and the cells were counted using a hemocytometer. Determination of the capacity of AMP-18 to initiate DNA synthesis was measured by the incorporation of [$^3$H]thymidine (Toback, 1980); to confirm the DNA synthesis assay, autoradiograms of leveled cells were counted (Kartha and Toback, 1985).

The protein AMP-18 is expressed in the antrum mucosa and to a lesser extent in the adjacent corpus mucosa. However, both antrum extracts and the active synthetic peptides stimulate proliferation of most simple epithelial cell lines. The major criterion used, apart from cells which might be natural targets for AMP-18 or its peptides, was that of growth control, particularly cell-density restriction. Many transformed stomach lines derived from human cancer patients are available from various sources, but most of these do not exhibit growth control. For example, a gastric AGS adenocarcinoma cell subline from Dr. Duane Smoot (Howard University College of Medicine) showed a greater degree of contact inhibition, and responded well to AMP-18 and its derived peptides. These cells do not naturally synthesize AMP-18. Similar responses were observed with the non-transformed rat IEC intestinal epithelial cells (provided by Dr. Mark Musch, Dept. Medicine, University of Chicago); the latter show excellent epithelial cell characteristics in culture (Quaroni et al., 1979; Digass et al., 1998).

18. Receptors for AMP-18 on the Surface of Epithelial Cells

Characterization of the target cell receptors of AMP-18 is intriguing because of the apparent existence of receptors on cells which are not expected ever to contact this protein. Initial growth response assays were performed on kidney-derived epithelial cell lines, which responded well to the stomach factor. Gastric cell lines, as well as the non-transformed rat intestinal epithelial IEC-6 cells, were used to address the receptors in cells that are likely the true physiological targets for the antrum factor. The specificity for the action of this protein in vivo likely arises from the extremely tissue specific nature of its expression, rather than that of its receptor. It is possible that AMP-18 may interact with receptors shared with other growth factors. However, the additive growth stimulus of EGF and the antrum extracts suggest that AMP-18 may have novel receptors.

Protein molecules in cell membranes that interact with AMP-18 may be sought in several different ways. Pure AMP-18 or related peptides labeled, e.g. with biotin or radioactive iodine, are used to estimate the number of saturatable sites on the cell surface. Scatchard analysis of the binding values as used to determine the number and affinity of receptors. For quantitative studies, binding is measured at increasing AMP ligand concentrations, and non-specific components are identified by measuring binding in the presence of excess unlabeled factor. Iodinated growth factors have been cross-linked to cellular receptors enabling their identification (Segarini et al., 1987). Labeled AMP ligands are incubated with cells, and the bound ligand is cross-linked to the receptors by disuccinimidyl suberate. The labeled proteins are resolved by SDS-PAGE, and autodiography is used to visualize the cross-linked complex permitting an estimate of the MW of the receptor(s). Synthetic peptide mimics or antagonists permit studies of the cellular receptors, and their properties are reasonably inferred prior to future definitive identification, presumably by cloning techniques.

In addition to crosslinking studies, antibodies, or his6-tagged AMP-18 or peptides are used to isolate cellular or mucus proteins which bind to AMP-18. As an additional approach, an immobilized AMP-18 affinity matrix can be created by using CNMBr-activated Sepharose. As a simple beginning to the analysis of the signal transduction pathway mediated by any cell receptor, a test to assay protein tyrosine kinase activity in affinity isolates is available (Yarden and Ullrich, 1988; Schlessinger and Ullrich, 1992).

19. Is AMP-18 Processed to Bioactive Peptides?

The functional molecular form(s) of AMP-18 is not known. Certainly, the ca. 18 kDa is the protein form which accumulates in antrum mucosal cells, and substantial amounts of polypeptides of lower MW are not detected with the antisera, even though they do react with pepsin fragments down to ca. 10 kDa and also with the bioactive peptide 78–119 (having only 42 amino acids). Having access to labeled or tagged AMP-18 enables a question of whether the protein is processed in antrum mucosal extracts, or by the epithelial cells which respond to it, to be explored.

20. Genes for AMP-18 in Man and Mouse

Using PCR techniques employing primers based on the sequence of the human cDNA clone, genomic clones of human and mouse preAMP-18 were obtained. The exon/intron structure (FIG. 13) is complete. Mouse AMP exons are sufficiently similar to those of human and pig to allow a sequence of the mouse gene to be assembled. Human and mouse genes have very similar structures, the mouse gene being slightly smaller. The ORF contained in exons of the mouse gene predicts a protein having 65% identity to the human and pig proteins. A 2 kb of sequence is upstream of the human gene.

21. Knockout of the AMP-18 Gene in Mouse

From the mouse map a targeting construct is designed. The construct preferably contains: [5'—TK (a functional thymidine kinase gene)—ca. 5 kb of the 5' end of AMP-18 DNA—the neomycin phosph-transferase (neo) gene under the control of the phosphoglycerate kinase (PGK) promoter—ca. 3 kb of the 3' end of the gene—3']. A considerable length of homology of the construct with the resident AMP-18 gene is required for efficient targeting. Increasing the total homology from 1.7 to 6.8 kb increases the efficiency of homologous targeting into the hrpt gene about 200-fold (Hasty et al., 1991). Beyond that total length, the efficiency increases only slightly. To facilitate the detection of homologous intergrants by a PCR reaction, it is useful to have the neo gene close to one end of the vector. The resulting transfectants can be provided by PCR with two primers, one in the neo gene and the other in the AMP-18 locus just outside of the targeting vector. Flanks extending 4 kb 5' and 4.5 kb 3' of the mouse gene have been obtained. Through homologous recombination, the coding region will be replaced by the neo gene to ensure a complete knockout of the gene are already cloned. After trimming off the plasmid sequence, the targeting cassette will be transfected into ES cells and stable transfectants obtained by selection with G418, an analog of neomycin, and gancyclovir (Mansour et al., 1988). Southern blots with the probe from the flanking sequence will be used to screen for targeted homologous recombinants. Correctly targeted ES cell clones will be injected in blastocysts from C57BL/6 mice.

Male offspring obtained from surrogate mothers that have at least 50% agouti coat (embryonic stem cell (ES) cell derived) are bred with C57BL/6 mice. F1 mice that are agouti have the paternal component derived from the ES cells (agouti is dominant over black). 50% of these mice should have the knockout preAMP-18 allele. These hemizygous mice are monitored for any effect of diminished gene dosage. Homozygous knockouts are preferable. If the sole function of AMP-18 is in the stomach following birth, then viable homozygotes are expected. If these cannot be obtained, a fetally lethal defect would be indicated, and the fetal stage of abortion would be ascertained. This result would suggest an unanticipated role of the protein in normal development.

Homozygous AMP-18 knockout mice are useful for investigations of stomach morphology and function. It is expected that such knockouts will show if AMP-18 is essential, and at which stage of gastro-intestinal development it is bioactive. It is possible that the AMP-18 knockout hemizygous mice will already show a phenotype. This could occur if reduced dosage of the protein reduces or eliminates its function, or if parental imprinting or random mono-allelic expression has a significant influence. A range of possible outcomes of the AMP-18 knockout in mice include: i) no viable homozygotes, implying an essential unanticipated developmental role; ii) viable homozygotes, but with obviously impaired gastrointestinal functions; iii) no strong phenotype, i.e. the protein is not important to the development and life of the laboratory mouse. If appropriate, the generation of AMP-18 in overexpressing mice is pursued. A truncated AMP-18 protein produced in the mice could potentially create a dominant negative phenotype; knowledge gained from the experiments will further define the functional domains of the protein.

| Abbreviations for amino acids | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isolceucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DOCUMENTS CITED

Aithal, N. H., et al. (1994) *Am. J. Physiol.* 266:F612–619.
Altschul, S., (1997) et al. (1994) *Nuc. Acids Res.* 25:3389–3402.
Baczako, K, et al. (1995) *J. Pathol.* 176:77–86.
Blaser, M. J. et al. (1987) *Gastroenterol.* 93:371–383
Boman, H. G. (1995) *Ann. Rev. Immunol.* 13:61–92.
Cohen, G. B., et al. (1995) *Cell* 80:237–248.
Cregg, J. M., et al. (1993) *Bio/Technol.* 11:905–910.

Dignass, A. U., et al. (1998) *Eur. J. clin. Invest.* 28:554–561
Falk, P., et al. (1993) *Proc. Nat. Acad. Sci.* 90:2035–2039.
Goodwin, C. S., et al., (1986) *J. Clin. Microbiol.* 39:353–356
Hasty, P., et al. (1991) *Mol. Cell. Biol.* 11:5586–5591.
Houston, M. E., et al. (1996) *Biochem.* 35:10041–10050.
Janknecht, R., et al. (1991) *Proc. Nat. Acad. Sci. USA* 88:8972–8976
Jeon, C. J., et al. (1994) *Proc. Nat. Acad. Sci. USA* 91:9106–9110
Johnson, F. R. and McMinn, R. M. H. (1970) *J. Anat.* 107:67–86.
Kartha, S. and Toback, F. G. (1985) *Am. J. Physiol.* 249:F967–F972
Kartha, S., et al. (1992) *Exp. Cell Res.* 200:219–226.
Lieske, J. C., et al. (1994) *Proc. Natl. Acad. Sci.* 91:6987–6991.
Lieske, J. C., et al. (1997) *Am. J. Physiol.* F224–F233.
Lacy, E. R. (1998) *J. Clin. Gastroenterol.* 10(Suppl 1):72–77.
Mansour, S., et al. (1988) *Nature* 336:348.
Moore, K. S., et al. (1991) *J. Biol. Chem.* 266:19851–19857.
Nguyen, J. T., et al. (1998) *Science* 282:2088–2092.
Nomura, A., et al. (1991) *N. engl. J. Med.* 325–1132–1136.
Nursat, A., et al. (1992) *J. Clin. Invest.* 89:1501–1511.
Park, C. B., et al. (1997) *FEBS Lett.* 411:173–178.
Parsonnet, J., et al. (1991) *N. Engl. J. Med.* 325:1127–1131.
Podolsky, D. K. (1997) *J. Gastroenterol.* 32:122–126.
Powell, C. J., (1987) Ph.D. Dissertation, University of Chicago.
Quaroni, A., et al. (1979) *J. Cell Biol.* 80:248–265.
Romanos, M. A., et al. (1992) *Yeast* 8:423–488.
Rotimi, V. O., et al. (1990) *Afr. J. Med. med. Sci.* 19:275–280.
Sands, B. E. and Podolsky, D. K. (1996) *Ann. Rev. Physiol.* 58:253.
Schlessinger, J. and Ullrich, A. (1992) *Neuron* 9:383–391.
Sears, I. B., et al. (1998) *Yeast* 14.
Segarini, P. R., et al. (1987) *J. Biol. Chem.* 262:14655–14662.
Smith, D. B. and Johnson, K. S. (1988) *Gene* 67:31–40.
Toback, F. G. (1980) *Proc. Nat. Acad. Sci.* 77:6654–6656.
Yarden et al. and Ullrich (1988) *Biochemistry* 27:3113–3119.
Yoo, O. J. et al. (1982) *PNAS* 79:1049–1053.
Yoshikawa, Y., et al. (2000) *Jap. J, Cancer Res.* 91:459–463.

---

What is claimed is:

1. A group of isolated cellular growth stimulating proteins designated gastrokines, said proteins produced by gastric epithelial cells and consisting of an amino acid sequence VKEK/QKRXXGKGPGGXPPK (SEQ ID NO: 1).

2. An isolated protein consisting of an ammo acid sequence from positions 21 to 185 of the sequence as shown in FIG. 8 (SEQ ID NO: 18), said protein present in pig gastric epithelia in a processed form lacking the 20 amino acids which constitute a signal peptide sequence.

3. A recombinant human protein comprising the amino acid sequence as in FIG. 3 (SEQ ID NO: 13).

4. A growth stimulating peptide derived from a protein consisting of an amino acid sequence VKEK/QKXXGKGPGGXPPK (SEQ ID NO:1).

5. A modified peptide produced by the method comprising the following steps:
   (a) eliminating major protease sites in an unmodified peptide consisting essentially of an amino acid sequence VKEK/QKXXGKGPGGXPPK (SEQ ID NO:1) by amino acid substitution or deletion in the unmodified peptide and
   (b) optionally introducing amino acid analogs of amino acids or D-amino acids in the unmodified peptide to produce a modified protein.

6. A synthetic growth stimulating peptide, having a sequence of amino acids as in positions 78 to 119 of the sequence shown in FIG. 3 (SEQ ID NO: 13).

7. A synthetic growth stimulating peptide having a sequence of ammo acids from position 97 to position 117 as shown in FIG. 3 (SEQ ID NO: 13).

8. A synthetic growth stimulating peptide consisting of a sequence of amino acids from position 97 to position 117 as shown in FIG. 3 (SEQ ID NO: 13).

9. A synthetic growth stimulating peptide consisting of a sequence of amino acids from position 97 to position 121 as shown in FIG. 3 (SEQ ID NO: 13).

10. A synthetic growth stimulating peptide consisting of a sequence of amino acids from position 104 to position 117 as shown in FIG. 3 (SEQ ID NO: 13).

* * * * *

UNITED STATES PATENT AND TRADEMARK OFFICE
CERTIFICATE OF CORRECTION

PATENT NO. : 6,734,289 B2  Page 1 of 1
APPLICATION NO. : 09/821726
DATED : May 11, 2004
INVENTOR(S) : Terence Martin et al.

It is certified that error appears in the above-identified patent and that said Letters Patent is hereby corrected as shown below:

In Column 13, Line 30, please delete the table and replace with the following table:

TABLE 1: BIOACTIVITY OF SYNTHETIC PEPTIDES BASED ON THE SEQUENCE OF GASTROKINE (AMP-18)

| Name of Peptide, Sequence in Human | #AA | AMINO ACID SEQUENCE | $K_{ID}, \mu M$ |
|---|---|---|---|
| 78-119 | 42 | KKTCIVHKMKKEVMPSIQSLDALVKEKKLQGKGPGGPPPKGL (SEQ ID NO: 6) | 0.3 |
| 78-88 | 11 | KKTCIVHKMKK (SEQ ID NO: 4) | Inactive |
| 87-105 | 19 | KKEVMPSIQSLDALVKEKK (SEQ ID NO: 5) | Inactive |
| 104-117 | 14 | KKLQGKGPGGPPPK (SEQ ID NO: 3) | 0.8 |
| 104-11 | 18 | KKLQGKGPGGPPPKGLMY (SEQ ID NO: 7) | 1.0 |
| 97-117 | 21 | LDALVKEKKLQGKGPGGPPPK (SEQ ID NO:8) | 0.3 |
| 97-117** | 21 | GKPLGQPGKVPKLDGKEPLAK (SEQ ID NO:9) | Inactive |
| 97-121 | 25 | LDALVKEKKLQGKGPGGPPPKGLMY (SEQ ID NO:10) | 0.2 |
| 109-117 | 9 | KGPGGPPPK (portion of SEQ ID NO:10) | 2.5 |
| 104-109 | 6 | KKLQGK (portion of SEQ ID NO:10) | 7.4 |
| 110-113 | 4 | GPGG (portion of SEQ ID NO: 10) | Inactive |
| mouse 97-119 | 23 | LDTMVKEQKGKGPGGAPPKDLMY (SEQ ID NO:2) | 0.2 |

Signed and Sealed this

Fifth Day of February, 2008

JON W. DUDAS
*Director of the United States Patent and Trademark Office*

UNITED STATES PATENT AND TRADEMARK OFFICE
CERTIFICATE OF CORRECTION

PATENT NO. : 6,734,289 B2
APPLICATION NO. : 09/821726
DATED : May 11, 2004
INVENTOR(S) : Terence Martin et al.

It is certified that error appears in the above-identified patent and that said Letters Patent is hereby corrected as shown below:

At Column 5, line 4,
"(SEQ ID NO: 1)" should read --(SEQ ID NO: 11)--

At Column 47, line 16, delete the text beginning with "VKEK/Q..." and ending with "...(SEQ ID NO: 1)" and replace with --VKEK/QKXXGKGPGGXPPK (SEQ ID NO: 1)--

At Column 48, claim 6 should read as follows:

6. A synthetic growth stimulating peptide, having a sequence of amino acids as in positions 78 to 119 of the sequence shown in FIG. 3 (SEQ ID NO: 13).

At Column 48, claim 7 should read as follows:

7. A synthetic growth stimulating peptide consisting of a sequence of amino acids from position 97 to position 117 as shown in FIG. 3 (SEQ ID NO: 13).

At Column 48, claim 8 should read as follows:

8. A synthetic growth stimulating peptide consisting of a sequence of amino acids from position 97 to position 121 as shown in FIG. 3 (SEQ ID NO: 13).

At Column 48, claim 9 should read as follows:

9. A synthetic growth stimulating peptide consisting of a sequence of amino acids from position 104 to position 117 as shown in FIG. 3 (SEQ ID NO: 13).

UNITED STATES PATENT AND TRADEMARK OFFICE
CERTIFICATE OF CORRECTION

PATENT NO. : 6,734,289 B2
APPLICATION NO. : 09/821726
DATED : May 11, 2004
INVENTOR(S) : Terence Martin et al.

It is certified that error appears in the above-identified patent and that said Letters Patent is hereby corrected as shown below:

At Column 48, claim 10 should read as follows:

10. An isolated bioactive peptide consisting of a sequence selected from the group consisting of LDTMVKEQKGKGPGGAPPKDLMY (SEQ ID NO: 2) and KKLQGKGPGGPPPK (SEQ ID NO: 3).

Signed and Sealed this

Twelfth Day of May, 2009

JOHN DOLL
*Acting Director of the United States Patent and Trademark Office*

SEQUENCE LISTING

```
<160> NUMBER OF SEQ ID NOS: 19

<210> SEQ ID NO 1
<211> LENGTH: 17
<212> TYPE: PRT
<213> ORGANISM: Unknown Organism
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<223> OTHER INFORMATION: Description of Unknown Organism: Illustrative
      peptide

<400> SEQUENCE: 1

Val Lys Glu Xaa Lys Xaa Xaa Gly Lys Gly Pro Gly Gly Xaa Pro
 1               5                  10                  15

Pro Lys

<210> SEQ ID NO 2
<211> LENGTH: 23
<212> TYPE: PRT
<213> ORGANISM: Mus sp.

<400> SEQUENCE: 2

Leu Asp Thr Met Val Lys Glu Gln Lys Gly Lys Gly Pro Gly Gly Ala
 1               5                  10                  15

Pro Pro Lys Asp Leu Met Tyr
                20

<210> SEQ ID NO 3
<211> LENGTH: 14
```

```
<212> TYPE: PRT
<213> ORGANISM: Homo sapiens

<400> SEQUENCE: 3

Lys Lys Leu Gln Gly Lys Gly Pro Gly Gly Pro Pro Lys
 1               5                  10

<210> SEQ ID NO 4
<211> LENGTH: 11
<212> TYPE: PRT
<213> ORGANISM: Homo sapiens

<400> SEQUENCE: 4

Lys Lys Thr Cys Ile Val His Lys Met Lys Lys
 1               5                  10

<210> SEQ ID NO 5
<211> LENGTH: 19
<212> TYPE: PRT
<213> ORGANISM: Homo sapiens

<400> SEQUENCE: 5

Lys Lys Glu Val Met Pro Ser Ile Gln Ser Leu Asp Ala Leu Val Lys
 1               5                  10                  15

Glu Lys Lys

<210> SEQ ID NO 6
<211> LENGTH: 42
<212> TYPE: PRT
<213> ORGANISM: Homo sapiens

<400> SEQUENCE: 6

Lys Lys Thr Cys Ile Val His Lys Met Lys Lys Glu Val Met Pro Ser
 1               5                  10                  15

Ile Gln Ser Leu Asp Ala Leu Val Lys Glu Lys Lys Leu Gln Gly Lys
                20                  25                  30

Gly Pro Gly Gly Pro Pro Lys Gly Leu
                35                  40

<210> SEQ ID NO 7
<211> LENGTH: 18
<212> TYPE: PRT
<213> ORGANISM: Homo sapiens

<400> SEQUENCE: 7

Lys Lys Leu Gln Gly Lys Gly Pro Gly Gly Pro Pro Lys Gly Leu
 1               5                  10                  15

Met Tyr

<210> SEQ ID NO 8
<211> LENGTH: 21
<212> TYPE: PRT
<213> ORGANISM: Homo sapiens

<400> SEQUENCE: 8

Leu Asp Ala Leu Val Lys Glu Lys Lys Leu Gln Gly Lys Gly Pro Gly
 1               5                  10                  15

Gly Pro Pro Lys
                20

<210> SEQ ID NO 9
<211> LENGTH: 21
```

```
<212> TYPE: PRT
<213> ORGANISM: Homo sapiens

<400> SEQUENCE: 9

Gly Lys Pro Leu Gly Gln Pro Gly Lys Val Pro Lys Leu Asp Gly Lys
 1               5                  10                  15

Glu Pro Leu Ala Lys
            20

<210> SEQ ID NO 10
<211> LENGTH: 25
<212> TYPE: PRT
<213> ORGANISM: Homo sapiens

<400> SEQUENCE: 10

Leu Asp Ala Leu Val Lys Glu Lys Lys Leu Gln Gly Lys Gly Pro Gly
 1               5                  10                  15

Gly Pro Pro Pro Lys Gly Leu Met Tyr
            20                  25

<210> SEQ ID NO 11
<211> LENGTH: 7995
<212> TYPE: DNA
<213> ORGANISM: Homo sapiens

<400> SEQUENCE: 11
agctttataa ccatgtgatc ccatcttatg gtttcaatcc atgcacagga ggaaaattgt      60
gggcacgaag tttccaaagg gaaaatttat agattggtag ttaatgaaat acagttttcc     120
tccttggcaa atttaattta ctagcttcac tgtataggaa aaagcaggaa aaaaattaaa     180
accaactcac ctccaaacct gttttgagct tttacttgtc tgcccaattg atagtttcta     240
ctctctgctt ttgatgaaaa tattttttat tattttaatg taacttctga aaactaaatt     300
atctagaagc aaataaaaag atattgcttt tatagttccc agaaggaaaa aacaaacact     360
aggaaagttc tatctatcag atgggggaga tgtgatggag gcagtgatat ttgagctgag     420
ccttgaacaa tgaacaggag tctaccaagc gagaggctag cgggtggccc tcaagataaa     480
acaacagcat gtacaaaggc atggagacat acacatcttg actcttccag gaatggtggg     540
aacgctggtg gagctagaat gtaggtacat agcataaagt ggcagacggg aagcctttgg     600
aaatcttatt acataggacc ctggatgcca ttccaatgac tttgaatttt ctgtaggctg     660
ccagcgaaat ttccaagcgt gatagagtca tgtctatcta tgcacttcag aaagacaacc     720
tcagggttaa tgaagaaaat gcattggaat ataagaaact ggtgaccaga gtgatcaatt     780
gcatgactgt tgtgaaagtc caggtgaggg gagctgtggg caaggtcaga gttgagaggc     840
atttcagaga taaatgaca gtaactaagt agatgtcagg ctgagaagaa agggctgtac     900
cagatatatg gtgctatcat taagtgagct caacattgca gaaaagggt aggtttggtg     960
ggagttgctc acaaaacatg tttagtctaa gcaaaaccat tgccatgggc tcagataaaa    1020
gttaagaagt ggaaaccatt cctacattcc tataggagct gctatctgga aggcctagta    1080
tacacgtggc ttttcagctg tgatttttgtt tgatttttagg gattattctt tttctgaatc    1140
tgagcaatgt tagcgtgtaa aatactcaca cccacagctt tgactgggtg agaagttatc    1200
ataaatcata ttgagtttgt tgtgataacct tcagcttcaa caagtgatga gtcaggtcaa    1260
ctccatgtga aagttccttg ctaagcatgc agatattctg aaaggtttcc tggtacactg    1320
gctcatggca cagataggag aaattgagga aggtaagtct ttgaccccac ctgataacac    1380
```

```
ctagtttgag tcaacctggt taagtacaaa tatgagaagg cttctcattc aggtccatgc   1440
ttgcctactc ctctgtccac tgctttcgtg aagacaagat gaagttcaca gtgagtagat   1500 ttttccttt gaatttacca ccaaatgatt ggagactgtc aatattctga gatttaggag   1560
gtttgcttct tatggcccca tcatggaaag tttgttttaa aaaaattctc tcttcaaaca   1620
catggacaca gagaggggaa caacacacac caggtcctgt tggggggtgg agagtgaggg   1680
gagggaactt agaggacagg tcaataggggg cagcaaacca ccatggcaca catatacca   1740 tgtaacaaac ctgcacgttc tgcacatgta tccctttttt ttagaagaag aaataatgaa   1800
aaaaaacctt ttttctattt atataatcat ggcatttata agcatctcta tagagaagga   1860
taattgtgct gagattagac agctgtctga gcacctcaca ctgacctatt tttaacaaaa   1920
tgactttcca catcacctga tttcggctcc atgcrggta agcagttcct aagccctaga   1980
aagtgccgat catccctcat tcttgaattc ctccttttat ttaccaaaat tcctgagcat   2040
gttcaggaaa gatgaaaagc ttattatcaa aataagtggc tgagatagac ttcttgtcac   2100
atttgttaca gtaaaatggg tctccaagaa agaaagattt gccttgggct ctagcatggc   2160
catttattta agaaagcatc tgaaacatga agctaccaca gcatctctcc tgtggttcca   2220
gacggaagcc tgagagtcta ggaggaggtg gaccgagaaa ccctgccaaa gtaactagta   2280
gtgccgggtt tctcacaaca cgatgcaaag gggctagaat cagatgacta ttttcatgtt   2340
tcaacatact acacactgga aaacgttacg gcagactcta ctttataatg gggctgcaaa   2400
tgtaaaatga ctactagaac taggtcctct taatagcagc aaagtttaaa agggtcagag   2460
ggagctccag acacaggtta gatttgattt ctctcctagt tctgctgtga acaagaggta   2520
taagtttggc caactcactt aaccctgaa gctcagttac cttatctgta aaatgattgc   2580
attgtactag gtgttctcta aaatttcttc tacctctgac ttttaggag actaattttt   2640 aactcctttt taagctattg ggagaaaaat ttaattttt ttcaaaagtt accttgaatc   2700
tctagagcag ttctcaaaac tattttgtcc caggcaaagg aaatgagact aggtacccag   2760
aatgaggcac cctgcataaa gctctgtgct ctgaaaacca atgtcaggga ccctgtgata   2820
aataattaaa ccaagtatcc tgggacactg ctagtgacat cgcctctgct gatcactctt   2880
gccagcgaga cactctatac ttgctttctc atcattggca tccaaactgc ctactaatcc   2940
attgctttgg aaagtttttt ttaataaaaa gattatttct attaggagga aaacatccca   3000
tgttaaatag gaaaattaac tgaaatcatt ttcagatgtg attttagca cttatagcca   3060 tttcaaacca tggtattcat ttatactatg ctatttattg taaaacttct ttttttttcc   3120
aaggaaaata agatagtttg ctttatttta aaacagtaac tttcttatat tggggcactg   3180
accaaaattc aatactggta caaatatgtt acctagggg tcaaaatatg tgccaggtga   3240
attttctgaa tttctctaaa gagagaattt taaaccttat aaaacaatta gaaacaagtg   3300
agtgagaggt gagcatcaac aacctgtgta acataagcca cagtacaaat ttaagctgaa   3360
taaccaagcc atgtcagtta tcccaaatca ttttgttaa tatttaggag gatacacata   3420
ttttcaataa cttaaaagtg aatctttact cctatctctt aatactcgaa gaagtataac   3480
tttcttcttt tactagattt aaataatcca aatatctact caaggtagga tgctgtcatt   3540
aactatagct gagtttatcc aaaatagaaa aatcatgaag atttataaag cattttaaaa   3600
ataatcattt atagcaagtc cttgaaagct ctaaataaga aaggcagttc tctactttct   3660
aataacacct atggtttata ttacataata taattcaaca aaacagcatt ctgaccaatg   3720
ataatttata ggaaattcat ttgccaagta tatgttttat tataaagtta atattttgac   3780
```

```
caatcttaaa aattttaaaa ctctattctg acatttccag aagtattatc ttagcaagtc   3840
atctttatga taccacttat taaactgaag agaaacaaga tggtacattc tgggttttac   3900
tttaaaaggg atttgattca ataatttgat ttatcactac ttgaaaatta cattttcttc   3960
ctcagactgg atggcaatga gatgaaagca gctttcctgg ctctcaactt cccttcttca   4020 tcaattttc cagcgtttca taaggcctac actaaaaatt ctaaaactat atatcacatt   4080
aatataatta cttataatta atcagcaatt tcacattatc gttaaaacct ttatggttaa   4140
aaaatgcaag gtaagagaag aaaaaaacac attgaactag aactgaacac attggtaaaa   4200
ttagtgaata cttttcataa gcttggatag aggaagaaag aagacatcat tttgccatgt   4260
aacaggagac caatgttatt tgtgatttca gattgtcttt gctggacttc ttggagtctt   4320
tctagctcct gccctagcta actatgtaag tctcaccttt tcaagtttgc taccaaaatg   4380
catttgcaag gaaatgtgat attaaatcac tctcaatctc ttataaactt cagaatatca   4440
acgtcaatga tgacaacaac aatgctggaa gtgggcagca gtcagtgagt gtcaacaatg   4500
aacacaatgt ggccaatgtt gacaataaca acggatggga ctcctggaat tccatctggg   4560
attatggaaa tgtaggtagt caacgtgcaa ttttcacttt attgtttaaa aatacgactt   4620
ctttttaaca aaaatgtgc atgttaacca taaagaaatt aaaaataaat tctaattaca   4680
catagcatac agttataagt aaaggtgacc attttgctca tccgattttg ttccctagag   4740
ataactactg ttaataagtg ttgcatgatc agttaaaatt caaaccaaca acactatgt   4800 tcaagggatt gtgggtatat acaacaaata tgaacatcct tttgccttgc ctgcagatac   4860
cctcaataat gctgaaagac ttatacaaca ttactgcttc caaagcttag actatctcac   4920
tttgttttca aggaggttt tacgaccttc taaagagatt gaaattgaca tttcacctaa   4980
aactcgggaa atgtaaatga caatattaat tggtaagaga ggaaagaaga agaaagaag   5040 gaaggaaaga aagaaagaag gaaggaagga aagaaagaaa gaaagaaaga aagagagaga   5100
aagaaagaaa aagaaaaag agagaaagag agaaggaaag aaagagagaa ggaaaggaaa   5160
agagaagcaa agaaagagag gagcaaagaa aggaacactt agcactagtt gggagaccca   5220
actctggaat tatcagctat atatttaaca aacgttatac ttttaaatag caaactcttt   5280
attgtttcaa ttttatctgg tcaattggaa aaataatttt tgtcttatct gtctccttga   5340
aatgtgagga tcaaaggaga ctaaaacatg atagctttta aagtctattt cagtaaaaca   5400
gacttatata gaggggtttt tatcatgctg gaacctggaa ataaagcaaa ccagttagat   5460
gctcagtctc tgccctcaca gaattgcagt ctgtccccac aaatgtcagc aatagatatg   5520
attgccaagc agtgccccat ccagtgctct tatcccagct catcacgatc ttggagttcc   5580
catttctctc tgcaggtgga actgacctct gataagaaaa gctcctcgga aacacatgc   5640 ctcactattt gccatctact ttaacagggc tttgctgcaa ccagactctt tcaaaagaag   5700
acatgcattg tgcacaaaat gaacaaggaa gtcatgccct ccattcaatc ccttgatgca   5760
ctggtcaagg aaaagaaggt aaaaataaaa ggcttttat ttttggtgag gggagaggtt   5820
ttacatcctt cagtaaataa cgagaagatc acagtcattc cctcttgact acagtatgtt   5880
gtagtgtgca gcacaagggg ggaagttatt ggtgattgcc tgagggaagg caacttctgc   5940
cacatcaaat gctgtggctc acacctacct ctacaaccgc tgagcaaagc acttgaaacc   6000
ttgactgtta gaggagcaaa gctctggtca caccaatagg agcctcagta ctttgccaag   6060
gacatttttc tgcaagagtt agttagggtt attagattta gcaaatgaaa atagaagata   6120
```

-continued

| | |
|---|---|
| tccagttagg tttgaattttt aggtaagcag caggtctttt tagtataata tatcctatgc | 6180 |
| aatatttggg atatactaaa aaaagatcca ttgttatctg aaattcaaat gtaactgggt | 6240 |
| attgtatatt ttgtctggcc atactaatcc aggtgagtgg aaagaagaga tccataatgt | 6300 |
| tttaaaatat ttgcctgagt tcatattcct ataactgata aatgagtacc tttcattgac | 6360 |
| aaggtagaga aaataaataa actgcattct cagaagatga ttattacata gtctaatcca | 6420 |
| aggaatctat gatgaccaaa tgaggtccaa gttgcagaat aaattaagcc tcagacttct | 6480 |
| gtgtttatga aagctgagg tttcaaacca ggtaaatccc ttaggacact tagaaatgct | 6540 |
| aagatataca gaataagcta gaaatggctc ttcttcatct tgattatgga aaaatttagc | 6600 |
| tgagcaacac tcactgttgg cctcgtatac ccctcaagtc aacaaaccac tgggcttggc | 6660 |
| attcattctc tcccattctt cctttctacc tctcttttcc acactcagct tcagggtaag | 6720 |
| ggaccaggag gaccacctcc caagggcctg atgtactcag tcaacccaaa caaagtcgat | 6780 |
| gacctgagca agttcggaaa aaacattgca acatgtgtc gtgggattcc aacatacatg | 6840 |
| gctgaggaga tgcaaggtga gtagcatccc tactgtgcac cccaagttag tgctggtggg | 6900 |
| attgtcagac tatcctcgcg cgtgtccata gtgggcacca gtgatgcagg gatggtcatc | 6960 |
| aaggccaaca tttgtgcagt gcttgctctg tgccaggtac tgttctatgt gctttaagtg | 7020 |
| tgttaactcg gttcttcaca gcaatcttat aggttctatt ttaatcctac tttatggatg | 7080 |
| aggaaactga ggtacagaga ggtcacaaaa tccttgcctg ggtcaattcc aagcattttg | 7140 |
| gctgtggatt ctgtgctctt aaatattatg gaacactgcc ttttaagtgt gaatcaagag | 7200 |
| tagactcaag tcatattcaa agaatgcat gaatggctaa atgaaagaag aatgctaata | 7260 |
| gaatctatta actttctata gctcagacaa tcacttaatt tctggacatt caagaacag | 7320 |
| ctgcacacaa acaaagtgtc tacctaggga cctaacttaa tggcaatttt ccagatctct | 7380 |
| gaattgattg atttcatcac aacaagtaga taaaccttga cattagcaca tagctagttt | 7440 |
| ggaaacccct actcccccaa tcccctccaa gaaaagagtc cttaaataga cattaatata | 7500 |
| ggcttcttct tttctctttta ttagaggcaa gcctgttttt ttactcagga acgtgctaca | 7560 |
| cgaccagtgt actatggatt gtggacattt ccttctgtgg agacacggtg gagaactaaa | 7620 |
| caatttttta aagccactat ggatttagtc atctgaatat gctgtgcaga aaaaatatgg | 7680 |
| gctccagtgg ttttttaccat gtcattctga aatttttctc tactagttat gtttgatttc | 7740 |
| tttaagtttc aataaaatca tttagcattg aattcagtgt atactcacat ttcttacaat | 7800 |
| ttcttatgac ttggaatgca caggatcaaa aatgcaatgt ggtggtggca agttgttgaa | 7860 |
| gtgcattaga ctcaactgct agcctatatt caagacctgt ctcctgtaaa gaacccttc | 7920 |
| aggtgcttca gacaccacta accacaaccc tgggaatggt tccaatactc tcctactcct | 7980 |
| ctgtccactg cttaa | 7995 |

<210> SEQ ID NO 12
<211> LENGTH: 752
<212> TYPE: DNA
<213> ORGANISM: Homo sapiens

<400> SEQUENCE: 12

| | |
|---|---|
| catgcttgcc tactcctctg tccactgctt tcgtgaagac aagatgaagt tcacaattgt | 60 |
| ctttgctgga cttcttggag tctttctagc tcctgcccta gctaactata atatcaacgt | 120 |
| caatgatgac aacaacaatg ctggaagtgg gcagcagtca gtgagtgtca acaatgaaca | 180 |
| caatgtggcc aatgttgaca ataacaacgg atgggactcc tggaattcca tctgggatta | 240 |

```
tggaaatggc tttgctgcaa ccagactctt tcaaagaag acatgcattg tgcacaaaat      300
gaacaaggaa gtcatgccct ccattcaatc ccttgatgca ctggtcaagg aaaagaagct      360
tcagggtaag ggaccaggag gaccacctcc caagggcctg atgtactcag tcaacccaaa      420
caaagtcgat gacctgagca agttcggaaa aaacattgca acatgtgtc gtgggattcc       480 aacatacatg gctgaggaga tgcaagaggc aagcctgttt ttttactcag gaacgtgcta      540
cacgaccagt gtactatgga ttgtggacat ttccttctgt ggagacacgg tggagaacta      600
aacaattttt taaagccact atggatttag tcatctgaat atgctgtgca gaaaaaatat      660
gggctccagt ggttttacc atgtcattct gaattttc tctactagtt atgtttgatt         720
tctttaagtt tcaataaat catttagcat tg                                     752
```

<210> SEQ ID NO 13
<211> LENGTH: 185
<212> TYPE: PRT
<213> ORGANISM: Homo sapiens

<400> SEQUENCE: 13

```
Met Lys Phe Thr Ile Val Phe Ala Gly Leu Leu Gly Val Phe Leu Ala
  1               5                  10                  15

Pro Ala Leu Ala Asn Tyr Asn Ile Asp Val Asn Asp Asn Asn
             20                  25                  30

Ala Gly Ser Gly Gln Gln Ser Val Ser Val Asn Glu His Asn Val
         35                  40                  45

Ala Asn Val Asp Asn Asn Asn Gly Trp Asp Ser Trp Asn Ser Ile Trp
     50                  55                  60

Asp Tyr Gly Asn Gly Phe Ala Ala Thr Arg Leu Phe Gln Lys Lys Thr
 65                  70                  75                  80

Cys Ile Val His Lys Met Lys Lys Glu Val Met Pro Ser Ile Gln Ser
                 85                  90                  95

Leu Asp Ala Leu Val Lys Glu Lys Lys Leu Gln Gly Lys Gly Pro Gly
            100                 105                 110

Gly Pro Pro Pro Lys Gly Leu Met Tyr Ser Val Asn Pro Asn Lys Val
        115                 120                 125

Asp Asp Leu Ser Lys Phe Gly Lys Asn Ile Ala Asn Met Cys Arg Gly
    130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175

Ser Phe Cys Gly Asp Thr Val Glu Asn
            180                 185
```

<210> SEQ ID NO 14
<211> LENGTH: 7280
<212> TYPE: DNA
<213> ORGANISM: Mus sp.
<220> FEATURE:
<221> NAME/KEY: modified_base
<222> LOCATION: (7084)
<223> OTHER INFORMATION: a, t, c, g. other or unknown
<220> FEATURE:
<221> NAME/KEY: modified_base
<222> LOCATION: (7138)
<223> OTHER INFORMATION: a, t, c, g. other or unknown

<400> SEQUENCE: 14

-continued

| | | | |
|---|---|---|---|
| gaattcaaac agcaggccat ctttcaccag cactatccga atctagccat accagcattc | 60 |
| tagaagagat gcaggcagtg agctaagcat cagacccctg cagccctgta agctccagac | 120 |
| catggagaag aggaaggttg tgggttcaag gagcttttca gagtggaaat ctgtggatca | 180 |
| gtgatttata aaacacagtt tccccctttat ttagatttga accaccagct tcagttgtag | 240 |
| aagagaacag gttaaaaaat aataagtgtc agtcagttct ccttcaaaac tattttaaac | 300 |
| gtttacttat tttgccaagt gacagtctct gcttcctctc ctaggagaag tcttccctta | 360 |
| ttttaatata atatttgaaa gttttcatta tctagagcag tggttctcat cctgtgggcc | 420 |
| atgagccctt tgggggggtt gaacgaccct tcacaggggg tcacatatca gatatcctgc | 480 |
| atcttagcta tttacattat gattcataac agtagcaaaa ttagttagga agtaggaaca | 540 |
| aaataacgtt atggttgtgg tcaccactat gttagagggt ccgcagcatt cagagggttg | 600 |
| agaactgttg ttctagaggc aaataagaag acagagttcc ttgatagggc ccagaggcag | 660 |
| tgaaagaagt ttccacgtag aaagtgaaga aggtctggtg tccgaagcag tgaggaactt | 720 |
| aaaaaaagaa aaccaaaaac attgccaact aacagtccag gagaagagcg gggcatgaaa | 780 |
| ggctgagttc ccatgggatg ccttgaatgg aatcagagtg tgggaaaatt ggtgtggctg | 840 |
| gaaggcaggt gccgggcatc tcagacgctg gtagctgggg aaacaggaaa cccctttagg | 900 |
| atcccaagat gccattccaa tgagcttgag atttttctca tggactgcca gtgaatgttt | 960 |
| ctacgctccg gaaattaatg tttacttatt ttccatattc tagggagaa ccctgggaaa | 1020 |
| aatggaggac attcattgaa atatctgagt cctgggataa ggcaggcttg gtcctacaac | 1080 |
| tctggtaaaa gtccatcagg aagtgccttg accaaggctg gagtggagag ctgttggtga | 1140 |
| gatgtaaggg caaggtttag ttgctagata tgtagatggc aagatggtgc tgccaacagc | 1200 |
| ccccagagct ctaacccact gagaaaccca ggaatgaatg atgggagatg gctttggtgc | 1260 |
| cagctgctag tgacatggct ggaaagctgc actggcttcg aggccagaca attcctcaag | 1320 |
| gaaacatctg gccagggtgc aagggccagt ttccttcctt ggagttcctt tcacagctaa | 1380 |
| gaacatcatc ccccaaccac tggttttgtt aaaaagtttt cagtatgact tgagcatggt | 1440 |
| caagaagcat agagaggggg aaataagggt ggaaggagct ggagaaagct tacaatagga | 1500 |
| ctgggtaaag ggaaggagaa gaaaccattc ccgcattccc ataggagcca gtaccaggaa | 1560 |
| gggcaggtgt acacacagat ctcatctaag gccatgtttg gtttagggat tactcttctc | 1620 |
| ccgaatctga gcagcagcaa tacgtaaaat acccacaccc atggcttcca tattccagaa | 1680 |
| cttatcacaa accgtgtaga gtttactgag ataccttcgt cagaggatga gtcagaggcc | 1740 |
| tcctgcctaa gggccctact gagcaggcag ctaaaggctt ccgggcctct gcagctccac | 1800 |
| agatacagga gagggaagca gataagccgt ggactccacc tgagcacacc tagcttgagc | 1860 |
| aaagctggtc aggtacaaat agcagagggc tgaatgtctg tgagcacgcc gcctgatcct | 1920 |
| ctgctccacc acactcctgc cgccatgaag ctcacagtaa gtcagatctt ctttttcaatg | 1980 |
| cagcaccata caacattaat agtcaggggt gaggggtct gactcttacg gcactgttac | 2040 |
| catagtggaa atattctcct ttcttttcat ggaatcatgg tgtttacaag catgtccata | 2100 |
| gagaagaaga attgccccgg aagagcctgt cacaggctga atactgtaga attgtctttc | 2160 |
| acaccatctg ttccaaggtt ctacttaaga cgagcagtct ctgggctcca gaaagagtct | 2220 |
| ttcttagcct tgatctcttt cttatttctg atttctcctt tcttatccat gatttccact | 2280 |
| tttaccagtt ctgggcatgt tccggtcaga ctggaagatc actgttgtca aaactagtct | 2340 |
| tcaacactct tggctgttaa catgaaaaca acggtccttg ggccctgtgc aagcatttct | 2400 |

```
tggagaaagt ctctggggat gaagctatct cagtttcccc actgaagtcc taggatacag    2460
aggctcaaac agagtgcaca tattcaattt cagcatactc tattggcgct gctttatgaa    2520
tcatatgaat ttatggaatt ggaaatgtaa actatgacca agaagcgtcc acctcagaac    2580
aggttgggtg gggaactcca agcacaggcc agagggctgc gtttctcttc tagttctgtc    2640
tagaggagtg gttctcgacc ttcctaatgc tgtgacccct taatacagtt cctcacgttg    2700
tcgtgactcc cagccataaa attactttca ttgctactgc ataactgtaa ttttgctacc    2760
attatgagtt gtaatgtaaa tatctgatat gcaagatacc agataaccta agaaacggtt    2820
gtttgacctt taaggggtc acaacccaca ggtggagaac tactggtcta gggtccttta    2880
cagtccttta gctgcctcat ttacaggaga taacatcatg ctcaaaaact ccctccacat    2940
ttggcttttt gggttgtttt gttttgtttt tcaagacagg gtttctctgt gtagccctgg    3000
ctgtcctgga actcaccttt gtagaccagg ctggcctcga actcagaaat ccgcctgctt    3060
ctgcctcctg agcgctggga ttaaaggcgt gcgccaccat gtctggctca catctggctt    3120
tttaagagac cgatttttaac ttcttgcatt gaaataaat atagtagaaa tgcttaacct    3180
actaagacaa taaaaacagg attccttctg ctaggaagaa cacgttccag actaaggaaa    3240
aaaacctttt cagggctttc attacactgt gccatgcact aattttatgt tttcttcatc    3300
agttttcagt gtctgaaatt cagtgtcaaa attctaagac tacatatgaa tatcattaca    3360
gtaactcagc aattctatgt taccagtaag ttttctgta gtttaaaaaa aaggtggaag    3420
aagaaagcac agatagttta gcacatgggt aaaatcagta actatttctg atgagcttgg    3480
tgaagatgct gtaaaccatg cgaccaccag tcctgttctc tgtgctttca gatgttcgtc    3540
gtgggtctgc ttggcctcct tgcagctcct ggttttgctt acgtaagtct cattttctg    3600 aagttcattg tcaaaactgc atttacagtg aaatgtgatc ttaagtcacc ctctgcttct    3660
tatgaacatt agacggtcaa catcaatggt aatgatgca atgtagacgg aagtggacag    3720
cattcggtga gcatcaatgg tgtgcacaac gtggccaata tcgacaacaa taacggctgg    3780
gactcctgga atagcctctg ggactatgaa aacgtatgta atggacacac agggtaaaga    3840
tatggtgtag ccaccaccca ttaaaatttc tgaggtgaat tctagctgtt catgaacatt    3900
aaaagctacc agtaaaagtg cccattccac tcaaaacaat tttactttt tgcatataat    3960 tattgctaat aagtattaca caataggtcg aaattcaaag ggatcaatag taaggataaa    4020
aactatgtac aaagacaaac acagcatcct ttggtcttcc ctgcagagag tctccatgat    4080
gttaaaggtc caatgttta tggaggctga atgaaatacg aatgcctctg tgatggaaaa    4140
ggcccaacat cttatggaga atgagtgaag tatgaatgct attagttgta agagaaggcg    4200
atgcaaagca acacttggca ccacctgcca attactactt tcctatttaa atgtagttta    4260
aaaagcaaag cctgtcttcc ctgcctcctg gaaacactgc ggatggaggt agaccaaggt    4320
atgacagcct ttaaaagttt gtcagcaaaa cactccccca tacacacata cacacaccct    4380
cctactacac tggaactgaa gcaaaggcag tgggttagat atatccaccc tctaagagtt    4440
tgcaggtcat ctatatatga tagccagaga cacaactgca ggacagccag actctgagca    4500
ctctccccag ctccttgtag ctctgtttca gtggtgactg tgacaagaa tcctggggaa    4560 cctgtgcctc actgttctct gtcttcttta atagagtttc gctgccacga gactcttctc    4620
caagaagtca tgcattgtgc acagaatgaa caaggatgcc atgccctccc ttcaggacct    4680
cgatacaatg gtcaaggaac agaaggtaaa gtcctgcctt cttctttgga gtgacaggaa    4740
```

```
gtcttacagt ctccagtaca cagtgaagtc accccattc cctctttggt ggagcatgac    4800
agcatgtttg tcatgataaa tgccacaaac atgtaaaact gttcagtgtc tgcctgaatg    4860
gagggtggct tccactgtgt cagatgccgt ggcccacatc tgcctctgca gggtccagta    4920
aagcactggc tatcttgagt gtcagagacc caaaggtctg tacattcag tacaagccct    4980 ccatatttca agggcacact cctacagtcg ttggggttat cagaactagc aaacatagag    5040
actggatttt cagatgaaaa gaaatccttt ttaaagtcta agtatgcctt atacaatgtt    5100
tgagatattc tcaatactaa aaaaaaaaaa attgttgctt gcttgaaaat caaatgtaac    5160
caagtgtcct atatccagtg tcaatcatgg ctgtagtaga tgggaagagg gagcccgtgg    5220
ttttcacagt cagacgcctg agttattctt ctaagtgata aattggttcc tataacaagc    5280
aagccagtga atataaataa gctctatctc agaagttatc ctgtagtgct accctagaat    5340
ctaagagagc aaaagtgctt caaatttcag aataagtttt gctttggact tctgttttc    5400 taaacaacta taacttcaaa ccatctaagc ctcgtgggac acttagaaat accaagccat    5460
tcaaagctag aattgtttct tcaccttact tgaaaacaaa atgacaacca aaaattgtcc    5520
ccactgccct tgtacatctt cagatcagta aagtcctggg ctcagggatc attcactttc    5580
tttctttcct ttcacactca acttcagggt aaagggcctg gaggagctcc tcccaaggac    5640
ttgatgtact ccgtcaaccc taccagagtg gaggacctga atacattcgg accaaagatt    5700
gctggcatgt gcaggggcat ccctacctat gtggccgagg agattccagg tgtgtaccct    5760
gagatgctgt atatcccaat gcagtactga gagagccatc agacactcta aagtgtgacc    5820
acagacggac caatcatgtg gattatcaga gcaaacactt gcttgctcct tgtcagacag    5880
ttgtccatgc ttcaaaagtt cattaaaaaa aatagttcac aggctcctca cagaaacctt    5940
agtagaatcc acagcttctg ctcttagtct tactttttag aaactgagac ccagagaaag    6000
gtcacaaaac ttttgtctgg ctcaggttct atgtctttaa cttaatagaa taccgtcttt    6060
ctgggtgggt gggctctaga gtaaacttca agtgagttca aggaaagcat gagaagtagg    6120
gaagaccaaa tgaaggaga atgccaatga aatctatcga ttctatagcg ccaatgctta    6180
actcctaggc gttcaaagaa tagtatccac aaggtgtcag cctaagatcc taatctaaca    6240
gcaagttttc agatctctga agtgaaaaga gaaagcaaga gaggaacaga gacagaaaca    6300
gtaagagaca gagaggcaga gacaaagaga cagggagaat agagagggat taaaattaat    6360
atatagttta gaaattacga ctcctcacag tccctgcaga gtcctaggat aggcactgat    6420
ttggacttct tttcttctca ctaggaccaa accagccttt gtactcaaag aagtgctaca    6480
cagctgacat actctggatt ctgcggatgt ccttctgtgg aacatcagtg gagacatact    6540
agaagtcaca ggaaaacaac ccgtgggctc tgaccatcgc aatgcttgat tatgagagtg    6600
ttctctgggg gttgtgatta gcttctttaa ggctcaataa acccacgtgg cagcacatcc    6660
agtttgtaat gacatgcctc atgacttcta tgggagtcca atgtggcacc tgccagcctg    6720
tattcaggac ctctccgcta taagcatccc ctccagagtt ttcaaatact acaaagcaca    6780
gcctgggttt gggctcagat aggccactgc tgcctgacta cattacagac aaacaagttt    6840
taaaagaaag aaaaaagagc tcagagtggc tggaatcagc aagggtgttt ttcctgcaag    6900
gagccagaag tatcaataat cacccaagga ggagacactg ggaatgagag actagaacac    6960
acgcctgcag atacggagaa cctcagcatt gccgctctct cccataactg cacaccccct    7020
tctgtaaact ctgcttcttt cttcacctg aagatggccc ttgcttttt ttattatagg    7080 acangataac tagaccagaa agtcaacctg actctctaca tttatatgtc ttcccagntc    7140
```

```
aagaaatatt atttactggt gaatggcact tctatattcc cttggttcaa taagtctaca    7200
ggatccattc attgacaggc caagagtgag atcacatgat acccaagcac atgggtcttt    7260
ccttgaagga gaaggatcca                                                7280
```

<210> SEQ ID NO 15
<211> LENGTH: 543
<212> TYPE: DNA
<213> ORGANISM: Mus sp.

<400> SEQUENCE: 15

```
atgttcgtcg tgggtctgct tggcctcctt gcagctcctg gttttgctta cacggtcaac     60
atcaatggta atgatggcaa tgtagacgga agtggacagc attcggtgag catcaatggt    120
gtgcacaacg tggccaatat cgacaacaat aacggctggg actcctggaa tagcctctgg    180
gactatgaaa acagtttcgc tgccacgaga ctcttctcca agaagtcatg cattgtgcac    240
agaatgaaca aggatgccat gccctccctt caggacctcg atacaatggt caaggaacag    300
aagggtaaag ggcctggagg agctcctccc aaggacttga tgtactccgt caaccctacc    360
agagtggagg acctgaatac attcggacca aagattgctg gcatgtgcag gggcatccct    420
acctatgtgg ccgaggagat tccaggacca aaccagcctt tgtactcaaa gaagtgctac    480
acagctgaca tactctggat tctgcggatg tccttttgtg aacatcagt ggagacatac     540 tag                                                                  543
```

<210> SEQ ID NO 16
<211> LENGTH: 184
<212> TYPE: PRT
<213> ORGANISM: Mus sp.

<400> SEQUENCE: 16

```
Met Lys Leu Thr Met Phe Val Val Gly Leu Leu Gly Leu Leu Ala Ala
 1               5                  10                  15

Pro Gly Phe Ala Tyr Thr Val Asn Ile Asn Gly Asn Asp Gly Asn Val
            20                  25                  30

Asp Gly Ser Gly Gln Gln Ser Val Ser Ile Asn Gly Val His Asn Val
        35                  40                  45

Ala Asn Ile Asp Asn Asn Asn Gly Trp Asp Ser Trp Asn Ser Leu Trp
    50                  55                  60

Asp Tyr Glu Asn Ser Phe Ala Ala Thr Arg Leu Phe Ser Lys Lys Ser
65                  70                  75                  80

Cys Ile Val His Arg Met Asn Lys Asp Ala Met Pro Ser Leu Gln Asp
                85                  90                  95

Leu Asp Thr Met Val Lys Glu Gln Lys Gly Lys Gly Pro Gly Gly Ala
            100                 105                 110

Pro Pro Lys Asp Leu Met Tyr Ser Val Asn Pro Thr Arg Val Glu Asp
        115                 120                 125

Leu Asn Thr Phe Gly Pro Lys Ile Ala Gly Met Cys Arg Gly Ile Pro
    130                 135                 140

Thr Tyr Val Ala Glu Glu Ile Pro Gly Pro Asn Gln Pro Leu Tyr Ser
145                 150                 155                 160

Lys Lys Cys Tyr Thr Ala Asp Ile Leu Trp Ile Leu Arg Met Ser Phe
                165                 170                 175

Cys Gly Thr Ser Val Glu Thr Tyr
            180
```

<210> SEQ ID NO 17
<211> LENGTH: 597
<212> TYPE: DNA
<213> ORGANISM: Porcine sp.

<400> SEQUENCE: 17

| | | | | | |
|---|---|---|---|---|---|
| atgcctgact | tctcacttca | ttgcattggt | gaagccaaga | tgaagttcac | aattgccttt | 60 |
| gctggacttc | ttggtgtctt | cctgactcct | gcccttgctg | actatagtat | cagtgtcaac | 120 |
| gacgacggca | acagtggtgg | aagtgggcag | cagtcagtga | gtgtcaacaa | tgaacacaac | 180 |
| gtggccaacg | ttgacaataa | caatggatgg | aactcctgga | atgccctctg | ggactataga | 240 |
| actggctttg | ctgtaaccag | actcttcgag | aagaagtcat | gcattgtgca | caaaatgaag | 300 |
| aaggaagcca | tgccctccct | tcaagccctt | gatgcgctgg | tcaaggaaaa | gaagcttcag | 360 |
| ggtaagggcc | caggggacc | acctcccaag | agcctgaggt | actcagtcaa | ccccaacaga | 420 |
| gtcgacaacc | tggacaagtt | tggaaaatcc | atcgttgcca | tgtgcaaggg | gattccaaca | 480 |
| tacatggctg | aagagattca | aggagcaaac | ctgatttcgt | actcagaaaa | gtgcatcagt | 540 |
| gccaatatac | tctggattct | taacatttcc | ttctgtggag | gaatagcgga | gaactaa | 597 |

<210> SEQ ID NO 18
<211> LENGTH: 185
<212> TYPE: PRT
<213> ORGANISM: Porcine sp.

<400> SEQUENCE: 18

Met Lys Phe Thr Ile Ala Phe Ala Gly Leu Leu Gly Val Phe Leu Thr
1               5                   10                  15

Pro Ala Leu Ala Asp Tyr Ser Ile Ser Val Asn Asp Asp Gly Asn Ser
            20                  25                  30

Gly Gly Ser Gly Gln Gln Ser Val Ser Val Asn Asn Glu His Asn Val
        35                  40                  45

Ala Asn Val Asp Asn Asn Gly Trp Asn Ser Trp Asn Ala Leu Trp
    50                  55                  60

Asp Tyr Arg Thr Gly Phe Ala Val Thr Arg Leu Phe Glu Lys Lys Ser
65                  70                  75                  80

Cys Ile Val His Lys Met Lys Lys Glu Ala Met Pro Ser Leu Gln Ala
                85                  90                  95

Leu Asp Ala Leu Val Lys Glu Lys Lys Leu Gln Gly Lys Gly Pro Gly
            100                 105                 110

Gly Pro Pro Lys Ser Leu Arg Tyr Ser Val Asn Pro Asn Arg Val
        115                 120                 125

Asp Asn Leu Asp Lys Phe Gly Lys Ser Ile Val Ala Met Cys Lys Gly
130                 135                 140

Ile Pro Thr Tyr Met Ala Glu Glu Ile Gln Gly Ala Asn Leu Ile Ser
145                 150                 155                 160

Tyr Ser Glu Lys Cys Ile Ser Ala Asn Ile Leu Trp Ile Leu Asn Ile
                165                 170                 175

Ser Phe Cys Gly Gly Ile Ala Glu Asn
            180                 185

<210> SEQ ID NO 19
<211> LENGTH: 6
<212> TYPE: PRT
<213> ORGANISM: Artificial Sequence
<220> FEATURE:

-continued

```
<223> OTHER INFORMATION: Description of Artificial Sequence: Synthetic
      His tag

<400> SEQUENCE: 19

His His His His His His
  1               5
```